(12) United States Patent
Smethurst et al.

(10) Patent No.: US 9,199,988 B2
(45) Date of Patent: Dec. 1, 2015

(54) DIHYDROQUINAZOLINONE ANALOGUES

(71) Applicants: Christian Smethurst, Vienna (AT); Harald Engelhardt, Ebreichsdorf (AT); Davide Gianni, Vienna (AT); Ulrich Reiser, Vienna (AT)

(72) Inventors: Christian Smethurst, Vienna (AT); Harald Engelhardt, Ebreichsdorf (AT); Davide Gianni, Vienna (AT); Ulrich Reiser, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/225,486

(22) Filed: Mar. 26, 2014

(65) Prior Publication Data

US 2014/0296230 A1 Oct. 2, 2014

(30) Foreign Application Priority Data

Mar. 27, 2013 (EP) .................................. 13161487

(51) Int. Cl.
*C07D 471/04* (2006.01)
*C07D 413/04* (2006.01)
*C07D 413/14* (2006.01)

(52) U.S. Cl.
CPC ............ *C07D 471/04* (2013.01); *C07D 413/04* (2013.01); *C07D 413/14* (2013.01)

(58) Field of Classification Search
CPC ........................... C07D 471/04; C07D 413/04
USPC ................. 514/230.5, 266.2, 266.22, 266.24, 514/264.1; 544/284, 92, 279
See application file for complete search history.

(56) References Cited

PUBLICATIONS

Duncan et al., The design and synthesis of 5- and 6-isoxazolylbenzimidazoles as selective inhibitors of the BET bromodomains, Med. Chem. Comm., 2013, vol. 4, No. 1, pp. 140-144.
Hewings et al.; Optimizationation of 3,5-Dimethylisoxazole Derivatives as potent Bromodomain Ligands, J. Med. Chem. 2013, vol. 56, No. 8, pp. 3217-3227.
Hewings et al., 3,5-Dimethylisoxazoles Act As Acetyl-lysine-mimetic Bromodomain Ligands, J Med Chem, 2011, 54, pp. 6761-6770.
International Search Report, form PCT/ISA/210, and written opinion, form PCT/ISA/237, for corresponding application PCT/EP2014/056081, date of mailing May 9, 2014.

*Primary Examiner* — Kahsay Habte
(74) *Attorney, Agent, or Firm* — Michael P. Morris; Alan R. Stempel

(57) ABSTRACT

The present invention encompasses compounds of general formula (I)

wherein the groups $R^1$ to $R^4$ and $A_1$ to $A_5$ have the meanings given in the claims and in the specification. The compounds of the invention are suitable for the treatment of diseases characterized by excessive or abnormal cell proliferation pharmaceutical preparations containing such compounds and their uses as a medicament.

9 Claims, No Drawings

DIHYDROQUINAZOLINONE ANALOGUES

This invention relates to compounds of the general formula (I)

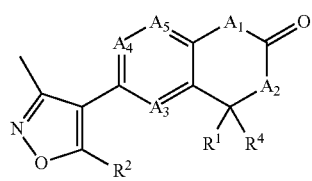

wherein the groups $R^1$ to $R^4$ and $A_1$ to $A_5$ have the meanings given in the claims and in the specification. The compounds of the invention are suitable for the treatment of diseases characterized by excessive or abnormal cell proliferation, pharmaceutical preparations containing such compounds and their uses as a medicament. The compounds of the invention are BRD4 inhibitors.

BACKGROUND OF THE INVENTION

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (about 110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRD-T) which contain tandem bromodomains capable of binding to two acetylated lysine residues in close proximity, increasing the specificity of the interaction. Recent research has established a compelling rationale for targeting BRD4 in cancer. BRD4 remains bound to transcriptional start sites of genes expressed during the entry into the G1 phase of the cell cycle, and is functioning to recruit the positive transcription elongation factor complex (P-TEFb), resulting in increased expression of growth promoting genes (Yang and Zhou, Mol. Cell. Biol. 28, 967, 2008). Importantly, BRD4 has been identified as a component of a recurrent t (15;19) chromosomal translocation in an aggressive form of human squamous carcinoma (French et al., Cancer Res. 63, 304, 2003). Such translocations express the tandem N-terminal bromodomains of BRD4 as an in-frame chimera with the NUT (nuclear protein in testis) protein, genetically defining the so-called NUT midline carcinoma (NMC). Functional studies in patient-derived NMC cell lines have validated the essential role of the BRD4-NUT oncoprotein in maintaining the proliferation and the differentiation block of these malignant cells. In addition, BRD4 has been identified as a critical sensitivity determinant in a genetically defined AML mouse model (Zuber et al., Nature 2011 478(7370):524-8). Suppression of BRD4 led to robust anti-leukemic effects in vitro and in vivo, accompanied by terminal myeloid differentiation. Interestingly, BRD4 inhibition triggered MYC down-regulation in a broad array of mouse and human leukemia cell lines examined, indicating that small molecule BRD4 inhibitors may provide a means to suppress the MYC pathway in a range of AML subtypes.

Finally, the other family members of the BET family have also been reported to have some function in controlling or executing aspects of the cell cycle, and have been shown to remain in complex with chromosomes during cell division—suggesting a role in the maintenance of epigenetic memory (Leroy et al, Mol. Cell. 2008 30(1):51-60).

Examples of bromodomain inhibitors are benzodiazepine derivatives, disclosed in WO2011/054553, and imidazo[4,5] quinoline derivatives, disclosed in WO2011/054846.

Thus, there is the need to provide BRD4 inhibitors useful for the prevention and/or treatment of diseases characterized by excessive or abnormal cell proliferation, such as cancer.

DETAILED DESCRIPTION OF THE INVENTION

The present invention relates to compounds of formula (I)

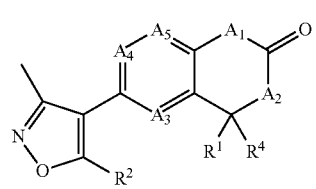

wherein,
$A_1$ is selected from —O—, —NH—, —N($C_{1-3}$ alkyl)-;
$A_2$ is selected from —O—, —N—$C_{1-3}$alkyl, wherein —$C_{1-3}$alkyl is optionally substituted with $R^5$;
$A_3$ is —N— or —C($R^3$)—,
$A_4$, $A_5$ is independently —N— or —CH—;
$R^1$ is 6 membered heteroaryl or phenyl, both of which groups can be optionally substituted with halogen;
$R^2$ is —H, —$C_{1-3}$alkyl or —O—$C_{1-3}$ alkyl;
$R^3$ is —H or —O—$C_{1-3}$ alkyl;
$R^4$ is —H or —$CH_3$;
$R^5$ is a 6 membered heterocycle or phenyl, each of which groups can be optionally substituted with —O—$C_{1-3}$alkyl or —$C_{1-3}$ alkyl;
wherein the compounds of formula (I) may be optionally be present in the form of salts.

In a preferred embodiment, the invention relates to compounds of formula (I), wherein $A_1$ is —NH— or —N($CH_3$)—. Preferably, $A_1$ is —NH—.

In a preferred embodiment, the invention relates to compounds of formula (I), wherein $A_2$ is selected from —N($CH_3$)—, —N(—$CH_2$(piperidinyl))-, —N(—$CH_2$(tetrahydrofuranyl))-, —N(benzyl)-, wherein the benzyl is optionally substituted with —O—$CH_3$ and wherein the piperidinyl is optionally substituted with —$CH_3$.

In a preferred embodiment, the invention relates to compounds of formula (I), wherein $R^1$ is phenyl, optionally substituted with halogen, or pyrdyl.

In a preferred embodiment, the invention relates to compounds of formula (I), wherein $A_3$, $A_4$ and $A_5$ are —CH—.

In a preferred embodiment, the invention relates to compounds of formula (I), wherein $R^3$.

In a further embodiment, the invention relates to compounds of formula (I) for use in the treatment of cancer.

In a further embodiment, the invention relates to compound of general formula (I) according to anyone of the embodiments described herein in the description and the claims—or the pharmaceutically acceptable salts thereof—for use in the treatment and/or prevention of cancer.

In a further embodiment, the invention relates to pharmaceutical preparation comprising as active substance one or more compounds of general formula (I) according to anyone of the embodiments described herein in the description and the claims optionally in combination with conventional excipients and/or carriers.

In a further embodiment, the invention relates to pharmaceutical preparation comprising a compound of general formula (I) according to anyone of the embodiments described herein in the description and the claims—or one of the pharmaceutically acceptable salts thereof—and at least one other cytostatic or cytotoxic active substance, different from formula (I).

The present invention further relates to hydrates, solvates, polymorphs, metabolites, derivatives and prodrugs of compounds of general formula (I).

The present invention further relates to a pharmaceutically acceptable salt of a compound of general formula (I) with anorganic or organic acids or bases.

In another aspect the invention relates to compounds of general formula (I)—or the pharmaceutically acceptable salts thereof—as medicaments.

In another aspect the invention relates to compounds of general formula (I)—or the pharmaceutically acceptable salts thereof—for use in a method for treatment of the human or animal body.

In another aspect the invention relates to compounds of general formula (I)—or the pharmaceutically acceptable salts thereof—for use in the treatment and/or prevention of cancer, infections, inflammations and autoimmune diseases.

In another aspect the invention relates to compounds of general formula (I)—or the pharmaceutically acceptable salts thereof—for use in a method for treatment and/or prevention of cancer, infections, inflammations and autoimmune diseases in the human and animal body.

In another aspect the invention relates to compounds of general formula (I)—or the pharmaceutically acceptable salts thereof—for use in the treatment and/or prevention of cancer.

In another aspect the invention relates to the use of the compounds of general formula (I)—or the pharmaceutically acceptable salts thereof—in the treatment and/or prevention of cancer.

In another aspect the invention relates to compounds of general formula (I)—or the pharmaceutically acceptable salts thereof—for use in a method for treatment and/or prevention of cancer in the human or animal body.

In another aspect the invention relates to compounds of general formula (I)—or the pharmaceutically acceptable salts thereof—for use in the treatment and/or prevention of hematopoietic malignancies, preferably AML, MM.

In another aspect the invention relates to compounds of general formula (I)—or the pharmaceutically acceptable salts thereof—for use in the treatment and/or prevention of solid tumors, preferably to lung, liver, colon, brain, thyroid, pancreas, breast, ovary and prostate cancer.

In another aspect the invention relates to a process for the treatment and/or prevention of cancer comprising administering a therapeutically effective amount of a compound of general formula (I)—or one of the pharmaceutically acceptable salts thereof—to a human being.

In another aspect the invention relates to a pharmaceutical preparation containing as active substance one or more compounds of general formula (I)—or the to pharmaceutically acceptable salts thereof—optionally in combination with conventional excipients and/or carriers.

In another aspect the invention relates to a pharmaceutical preparation comprising a compound of general formula (I)—or one of the pharmaceutically acceptable salts thereof—and at least one other cytostatic or cytotoxic active substance, different from formula (I).

Definitions

Terms that are not specifically defined here have the meanings that are apparent to the skilled man in the light of the overall disclosure and the context as a whole.

As used herein, the following definitions apply, unless stated otherwise.

In the groups, radicals, or moieties defined below, the number of carbon atoms is often specified preceding the group, for example, —$C_{1-5}$alkyl means an alkyl group or radical having 1 to 5 carbon atoms. In general, for groups comprising two or more subgroups, the first named sub-group is the radical attachment point, for example the substitutent —$C_{1-5}$ alkyl-$C_{3-10}$cylcoalkyl, means a $C_{3-10}$cylcoalkyl group which is bound to a $C_{1-5}$alkyl, the latter of which is bound to the core structure or to the group to which the substitutent is attached.

The indication of the number of members in groups that contain one or more heteroatom(s) (heteroalkyl, heteroaryl, heteroarylalkyl, heterocyclyl, heterocycylalkyl) relates to the total atomic number of all the ring members or chain members or the total of all the ring and chain members.

The person skilled in the art will appreciate that substituent groups containing a nitrogen atom can also be indicated as amine or amino. Similarly, groups containing oxygen atom can also be indicated with -oxy, like for example alkoxy. Groups containing —C(O)— can also be indicated as carboxy; groups containing —NC(O)— can also be indicated as amide; groups containing —NC(O)N— can also be indicated as urea; groups containing —NS(O)$_2$— can also be indicated as sulfonamide.

Alkyl denotes monovalent, saturated hydrocarbon chains, which may be present in both linear and branched form. If an alkyl is substituted, the substitution may take place independently of one another, by mono- or polysubstitution in each case, on all the hydrogen-carrying carbon atoms.

The term "$C_{1-5}$-alkyl" includes for example methyl (Me; —CH$_3$), ethyl (Et; —CH$_2$CH$_3$), 1-propyl (n-propyl; n-Pr; —CH$_2$CH$_2$CH$_3$), 2-propyl (i-Pr; iso-propyl; —CH(CH$_3$)$_2$), 1-butyl (n-butyl; n-Bu; —CH$_2$CH$_2$CH$_2$CH$_3$), 2-methyl-1-propyl (iso-butyl; i-Bu; —CH$_2$CH(CH$_3$)$_2$), 2-butyl (sec-butyl; sec-Bu; —CH(CH$_3$)CH$_2$CH$_3$), 2-methyl-2-propyl (tert-butyl; t-Bu; —C(CH$_3$)$_3$), 1-pentyl (n-pentyl; —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 3-methyl-1-butyl (iso-pentyl; —CH$_2$CH$_2$CH(CH$_3$)$_2$), 2-methyl-2-butyl (—C(CH$_3$)$_2$CH$_2$CH$_3$), 3-methyl-2-butyl (—CH(CH$_3$)CH (CH$_3$)$_2$), 2,2-dimethyl-1-propyl (neo-pentyl; —CH$_2$C (CH$_3$)$_3$), 2-methyl-1-butyl (—CH$_2$CH(CH$_3$)CH$_2$CH$_3$).

By the terms propyl, butyl, pentyl, etc. without any further definition are meant saturated hydrocarbon groups with the corresponding number of carbon atoms, wherein all isomeric forms are included.

The above definition for alkyl also applies if alkyl is a part of another group such as for example $C_{x-y}$-alkylamino or $C_{x-y}$-alkyloxy or $C_{x-y}$-alkoxy, wherein $C_{x-y}$-alkyloxy and $C_{x-y}$-alkoxy indicate the same group.

The term alkylene can also be derived from alkyl. Alkylene is bivalent, unlike alkyl, and requires two binding partners. Formally, the second valency is produced by removing a hydrogen atom in an alkyl. Corresponding groups are for example —CH$_3$ and —CH$_2$, —CH$_2$CH$_3$ and —CH$_2$CH$_2$ or >CHCH$_3$ etc.

The term "$C_{1-4}$-alkylene" includes for example —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CHCH(CH$_3$)$_2$)— and —C(CH$_3$)(CH$_2$CH$_3$)—.

Other examples of alkylene are methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene, etc.

By the generic terms propylene, butylene, pentylene, hexylene etc. without any further definition are meant all the conceivable isomeric forms with the corresponding number of carbon atoms, i.e. propylene includes 1-methylethylene and butylene includes 1-methylpropylene, 2-methylpropylene, 1,1-dimethylethylene and 1,2-dimethylethylene.

The above definition for alkylene also applies if alkylene is part of another group such as for example in HO—$C_{x-y}$-alkylenamino or H$_2$N—$C_{x-y}$-alkylenoxy.

Unlike alkyl, alkenyl consists of at least two carbon atoms, wherein at least two adjacent carbon atoms are joined together by a C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another group such as for example in $C_{x-y}$-alkenylamino or $C_{x-y}$-alkenyloxy.

Unlike alkylene, alkenylene consists of at least two carbon atoms, wherein at least two adjacent carbon atoms are joined together by a C—C double bond. If in an alkylene as hereinbefore defined having at least two carbon atoms, two hydrogen atoms at adjacent carbon atoms are formally removed and the free valencies are saturated to form a second bond, the corresponding alkenylene is formed.

Examples of alkenylene are ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene, hexenylene etc.

By the generic terms propenylene, butenylene, pentenylene, hexenylene etc. without any further definition are meant all the conceivable isomeric forms with the corresponding number of carbon atoms, i.e. propenylene includes 1-methylethenylene and butenylene includes 1-methylpropenylene, 2-methylpropenylene, 1,1-dimethylethenylene and 1,2-dimethylethenylene.

Alkenylene may optionally be present in the cis or trans or E or Z orientation with regard to the double bond(s).

The above definition for alkenylene also applies when alkenylene is a part of another group as in for example HO—$C_{x-y}$-alkenylenamino or H$_2$N—$C_{x-y}$-alkenylenoxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl.

By the generic terms propynyl, butynyl, pentynyl, etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl.

If a hydrocarbon chain carries both at least one double bond and also at least one triple bond, by definition it belongs to the alkynyl subgroup.

The above definition for alkynyl also applies if alkynyl is part of another group, as in $C_{x-y}$-alkynylamino or $C_{x-y}$-alkynyloxy, for example.

Unlike alkylene, alkynylene consists of at least two carbon atoms, wherein at least two adjacent carbon atoms are joined together by a C—C triple bond. If in an alkylene as hereinbefore defined having at least two carbon atoms, two hydrogen atoms in each case at adjacent carbon atoms are formally removed and the free valencies are saturated to form two further bonds, the corresponding alkynylene is formed.

Examples of alkynylene are ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene, hexynylene etc.

By the generic terms propynylene, butynylene, pentynylene, etc. without any further definition are meant all the conceivable isomeric forms with the corresponding number of carbon atoms, i.e. propynylene includes 1-methylethynylene and butynylene includes 1-methylpropynylene, 2-methylpropynylene, 1,1-dimethylethynylene and 1,2-dimethylethynylene.

The above definition for alkynylene also applies if alkynylene is part of another group, as in HO—$C_{x-y}$-alkynyleneamino or H$_2$N—$C_{x-y}$-alkynyleneoxy, for example.

By heteroatoms are meant oxygen, nitrogen and sulphur atoms.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —CI=$CH_2$, —C≡C—$CF_3$, —$CHFCH_2CH_3$, —$CHFCH_2CF_3$ etc.

From the previously defined haloalkyl (haloalkenyl, haloalkynyl) are also derived the terms haloalkylene (haloalkenylene, haloalkynylene). Haloalkylene (haloalkenyl, haloalkynyl), unlike haloalkyl, is bivalent and requires two binding partners. Formally, the second valency is formed by removing a hydrogen atom from a haloalkyl.

Corresponding groups are for example —$CH_2F$ and —CHF—, —$CHFCH_2F$ and —CHFCHF— or >$CFCH_2F$ etc.

The above definitions also apply if the corresponding halogen groups are part of another group.

Halogen relates to fluorine, chlorine, bromine and/or iodine atoms.

Cycloalkyl is made up of the subgroups monocyclic hydrocarbon rings, bicyclic hydrocarbon rings and spiro-hydrocarbon rings. The systems are saturated. In bicyclic hydrocarbon rings two rings are joined together so that they have at least two carbon atoms together. In spiro-hydrocarbon rings a carbon atom (spiroatom) belongs to two rings together. If a cycloalkyl is to be substituted, the substitutions may take place independently of one another, in the form of mono- or polysubstitutions in each case, on all the hydrogen-carrying carbon atoms.

Cycloalkyl itself may be linked as a substituent to the molecule via every suitable position of the ring system.

Examples of cycloalkyl are cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthalene), bicyclo[2.2.1]heptyl (norbornyl), bicyclo[4.1.0]heptyl (norcaranyl), bicyclo-[3.1.1]heptyl (pinanyl), spiro[2.5]octyl, spiro[3.3]heptyl etc. The above definition for cycloalkyl also applies if cycloalkyl is part of another group as in $C_{x-y}$-cycloalkylamino or $C_{x-y}$-cycloalkyloxy, for example.

If the free valency of a cycloalkyl is saturated, then an alicyclic group is obtained. The term cycloalkylene can thus be derived from the previously defined cycloalkyl. Cycloalkylene, unlike cycloalkyl, is bivalent and requires two binding partners. Formally, the second valency is obtained by removing a hydrogen atom from a cycloalkyl. Corresponding groups are for example cyclohexyl and

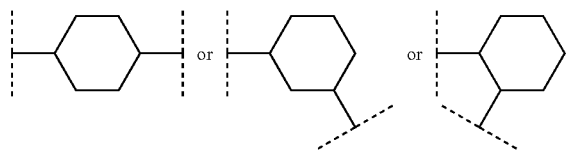

(cyclohexylene).

The above definition for cycloalkylene also applies if cycloalkylene is part of another group as in HO—$C_{x-y}$-cycloalkyleneamino or $H_2N$—$C_{x-y}$-cycloalkyleneoxy, for example.

Cycloalkenyl is also made up of the subgroups monocyclic hydrocarbon rings, bicyclic hydrocarbon rings and spiro-hydrocarbon rings. However, the systems are unsaturated, i.e. there is at least one C—C double bond but no aromatic system. If in a cycloalkyl as hereinbefore defined two hydrogen atoms at adjacent cyclic carbon atoms are formally removed and the free valencies are saturated to form a second bond, the corresponding cycloalkenyl is obtained. If a cycloalkenyl is to be substituted, the substitutions may take place independently of one another, in the form of mono- or polysubstitutions in each case, on all the hydrogen-carrying carbon atoms. Cycloalkenyl itself may be linked as a substituent to the molecule via every suitable position of the ring system.

Examples of cycloalkenyl are cycloprop-1-enyl, cycloprop-2-enyl, cyclobut-1-enyl, cyclobut-2-enyl, cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl, cyclohept-4-enyl, cyclobuta-1,3-dienyl, cyclopenta-1,4-dienyl, cyclopenta-1,3-dienyl, cyclopenta-2,4-dienyl, cyclohexa-1,3-dienyl, cyclohexa-1,5-dienyl, cyclohexa-2,4-dienyl, cyclohexa-1,4-dienyl, cyclohexa-2,5-dienyl, bicyclo[2.2.1]hepta-2,5-dienyl (norborna-2,5-dienyl), bicyclo[2.2.1]hept-2-enyl (norbornenyl), spiro[4.5]dec-2-ene etc.

The above definition for cycloalkenyl also applies when cycloalkenyl is part of another group as in $C_{x-y}$-cycloalkenylamino or $C_{x-y}$-cycloalkenyloxy, for example. If the free valency of a cycloalkenyl is saturated, then an unsaturated alicyclic group is obtained.

The term cycloalkenylene can thus be derived from the previously defined cycloalkenyl. Cycloalkenylene, unlike cycloalkenyl, is bivalent and requires two binding partners. Formally the second valency is obtained by removing a hydrogen atom from a cycloalkenyl. Corresponding groups are for example cyclopentenyl and

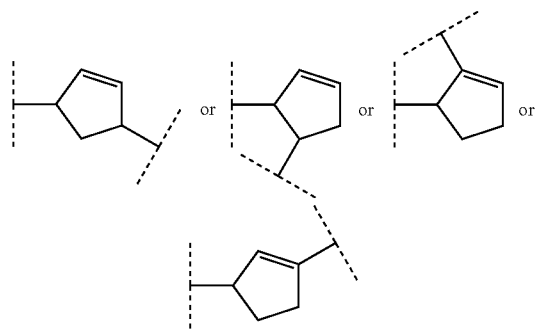

(cyclopentenylene) etc.

The above definition for cycloalkenylene also applies when cycloalkenylene is part of another group as in HO—$C_{x-y}$-cycloalkenyleneamino or $H_2N$—$C_{x-y}$-cycloalkenyleneoxy, for example.

Aryl denotes a mono-, bi- or tricyclic group with at least one aromatic carbocycle. Preferably it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated. If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc.

The above definition of aryl also applies when aryl is part of another group as in arylamino or aryloxy, for example.

If the free valency of an aryl is saturated, then an aromatic group is obtained. The term arylene can also be derived from the previously defined aryl. Arylene, unlike aryl, is bivalent and requires two binding partners. Formally, the second valency is formed by removing a hydrogen atom from an aryl. Corresponding groups are e.g. phenyl and

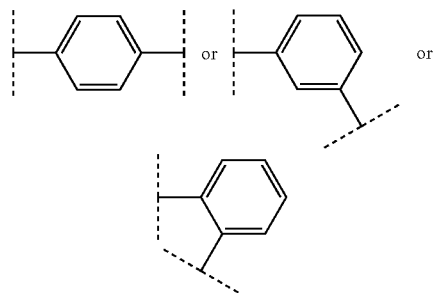

(o, m, p-phenylene), naphthyl and

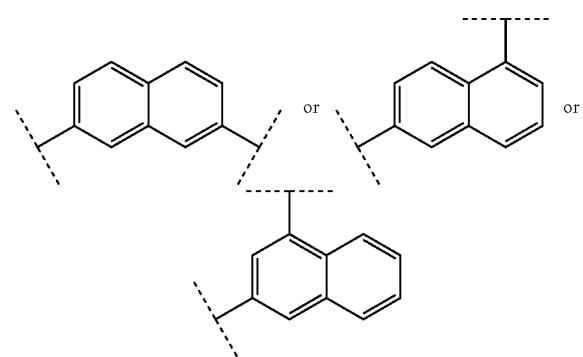

etc. The above definition for arylene also applies when arylene is part of another group as in HO-aryleneamino or H$_2$N-aryleneoxy for example.

Heterocyclyl or heterocycle denotes ring systems, which are derived from the previously defined cycloalkyl, cycloalkenyl and aryl by replacing one or more of the groups —CH$_2$— independently of one another in the hydrocarbon rings by the groups —O—, —S— or —NH— or by replacing one or more of the groups =CH— by the group =N—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur→sulphoxide —SO, sulphone —SO$_2$—; nitrogen→N-oxide).

A direct result of the derivation from cycloalkyl, cycloalkenyl and aryl is that heterocyclyl is made up of the subgroups monocyclic heterorings, bicyclic heterorings, tricyclic heterorings and spiro-heterorings, which may be present in saturated or unsaturated form. Saturated and unsaturated, non aromatic, heterocyclyl are also defined as heterocycloalkyl. By unsaturated is meant that there is at least one double bond in the ring system in question, but no heteroaromatic system is formed. In bicyclic heterorings two rings are linked together so that they have at least two (hetero)atoms in common. In spiro-heterorings a carbon atom (spiroatom) belongs to two rings together. If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

When the heterocyclyl has a nitrogen atom, the preferred position to bind the heterocyclyl substituent to the molecule is the nitrogen atom.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-5-oxide, to thiomorpholinyl-S,S-dioxide, 1,3-dioxolanyl, tetrahydropyranyl, tetrahydrothiopyranyl, [1.4]-oxazepanyl, tetrahydrothienyl, homothiomorpholinyl-S,S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-5-oxide, tetrahydrothienyl-S, S-dioxide, homothiomorpholinyl-S-oxide, 2,3-dihydroazet, 2H-pyrrolyl, 4H-pyranyl, 1,4-dihydropyridinyl, 8-azabicyclo[3.2.1]octyl, 8-azabicyclo[5.1.0]octyl, 2-oxa-5-azabicyclo[2.2.1]-heptyl, 8-oxa-3-aza-bicyclo [3.2.1]octyl, 3,8-diaza-bicyclo[3.2.1]octyl, 2,5-diaza-bicyclo-[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, 1,4-dioxa-spiro[4.5]-decyl, 1-oxa-3.8-diaza-spiro[4.5]decyl, 2,6-diaza-spiro[3.3]heptyl, 2,7-diaza-spiro[4.4]nonyl, 2,6-diaza-spiro[3.4]octyl, 3,9-diaza-spiro [5.5]undecyl, 2.8-diaza-spiro[4.5]decyl etc.

Further examples are the structures illustrated below, which may be attached via each hydrogen-carrying atom (exchanged for hydrogen):

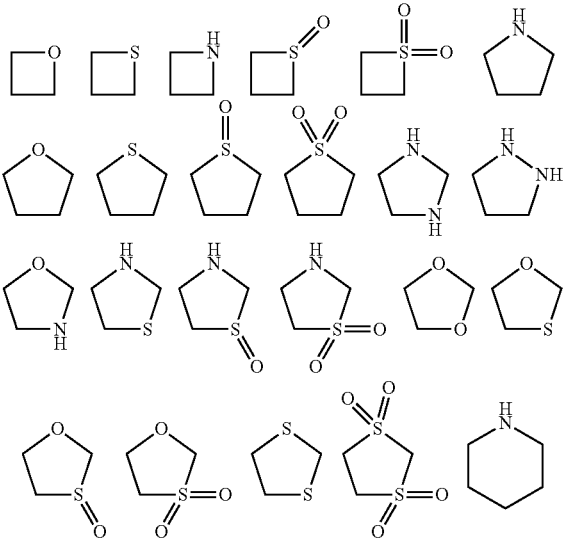

-continued
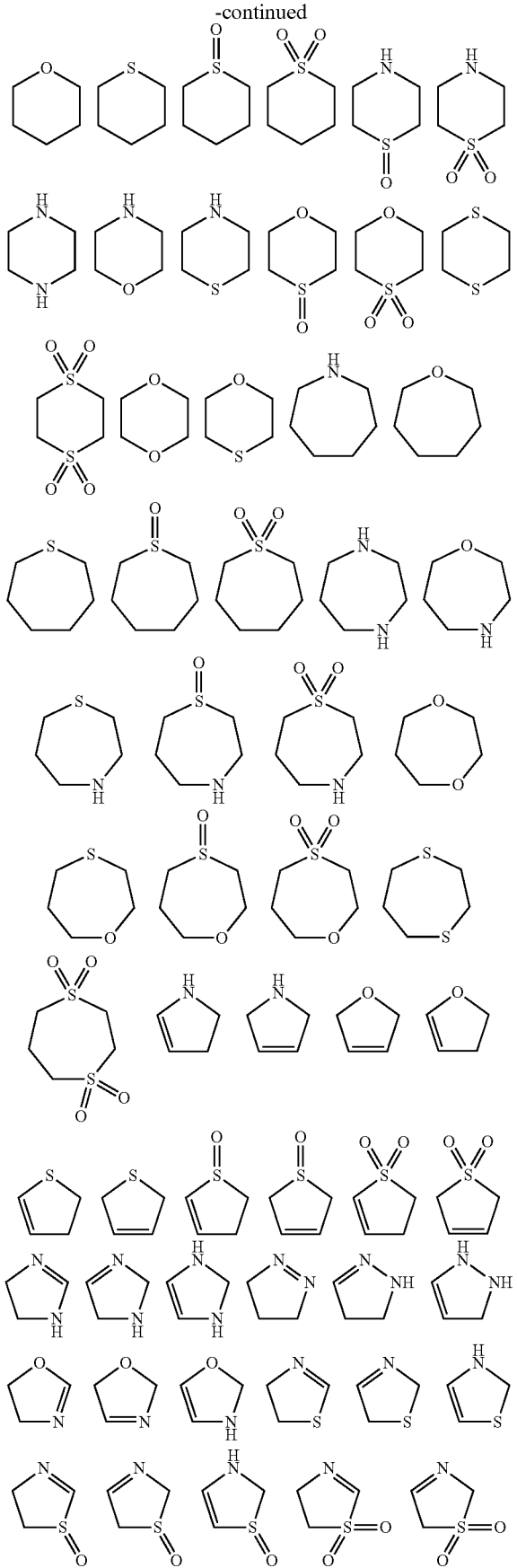
-continued
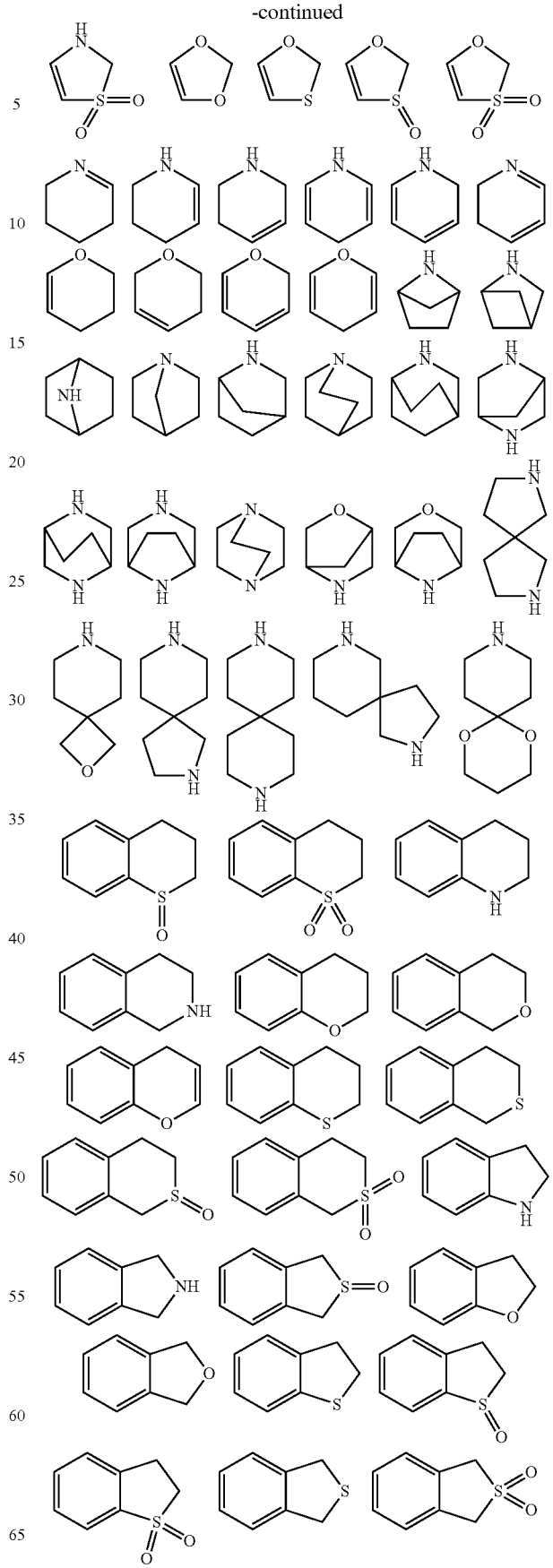

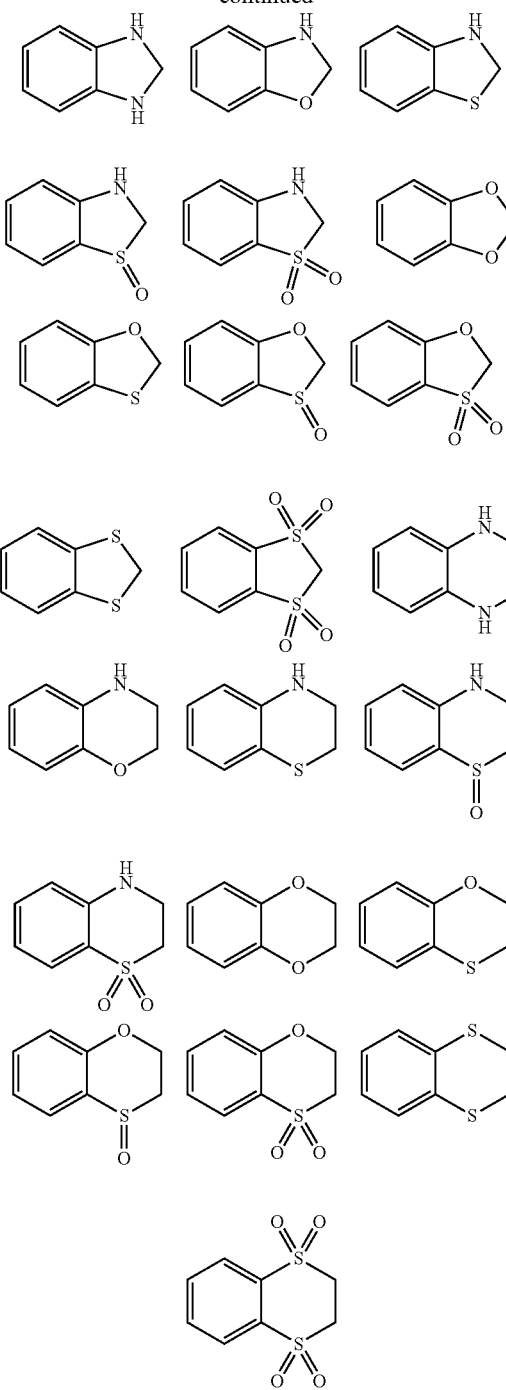

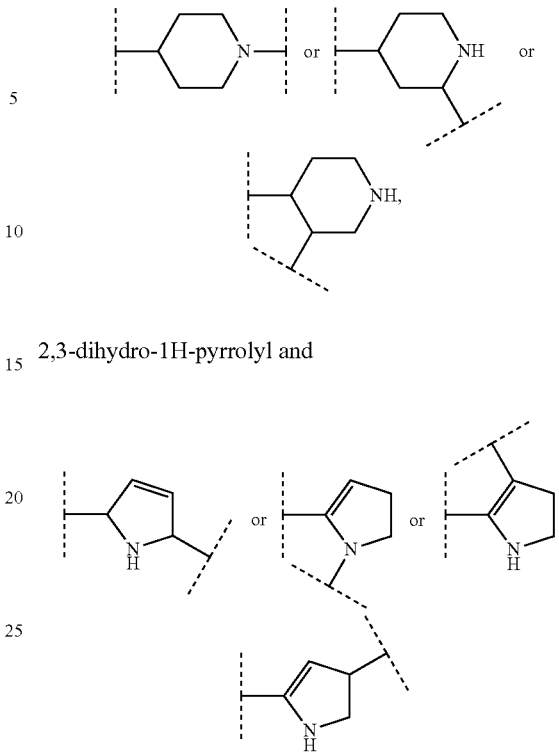

2,3-dihydro-1H-pyrrolyl and etc.

The above definition of heterocyclylene also applies if heterocyclylene is part of another group as in HO-heterocyclyleneamino or H₂N-heterocyclyleneoxy for example.

Heteroaryl denotes monocyclic heteroaromatic rings or polycyclic rings with at least one heteroaromatic ring, which compared with the corresponding aryl or cycloalkyl (cycloalkenyl) contain, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system. If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, triazinyl, pyridyl-N-oxide, pyrrolyl-N-oxide, pyrimidinyl-N-oxide, pyridazinyl-N-oxide, pyrazinyl-N-oxide, imidazolyl-N-oxide, isoxazolyl-N-oxide, oxazolyl-N-oxide, thiazolyl-N-oxide, oxadiazolyl-N-oxide, thiadiazolyl-N-oxide, triazolyl-N-oxide, tetrazolyl-N-oxide, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, purinyl, pteridinyl, benzothiazolyl, imidazothiazolyl, imidazothiazolyl, quinolinyl-N-oxide, indolyl-N-oxide, isoquinolyl-N-oxide, quinazolinyl-N-oxide, quinoxalinyl-N-oxide, The above definition of heterocyclyl also applies if heterocyclyl is part of another group as in heterocyclylamino or heterocyclyloxy for example.

If the free valency of a heteroyclyl is saturated, then a heterocyclic group is obtained.

The term heterocyclylene is also derived from the previously defined heterocyclyl. Heterocyclylene, unlike heterocyclyl, is bivalent and requires two binding partners. Formally, the second valency is obtained by removing a hydrogen atom from a heterocyclyl. Corresponding groups are for example piperidinyl and phthalazinyl-N-oxide, indolizinyl-N-oxide, indazolyl-N-oxide, benzothiazolyl-N-oxide, benzimidazolyl-N-oxide etc.

Further examples are the structures illustrated below, which may be attached via each hydrogen-carrying atom (exchanged for hydrogen):

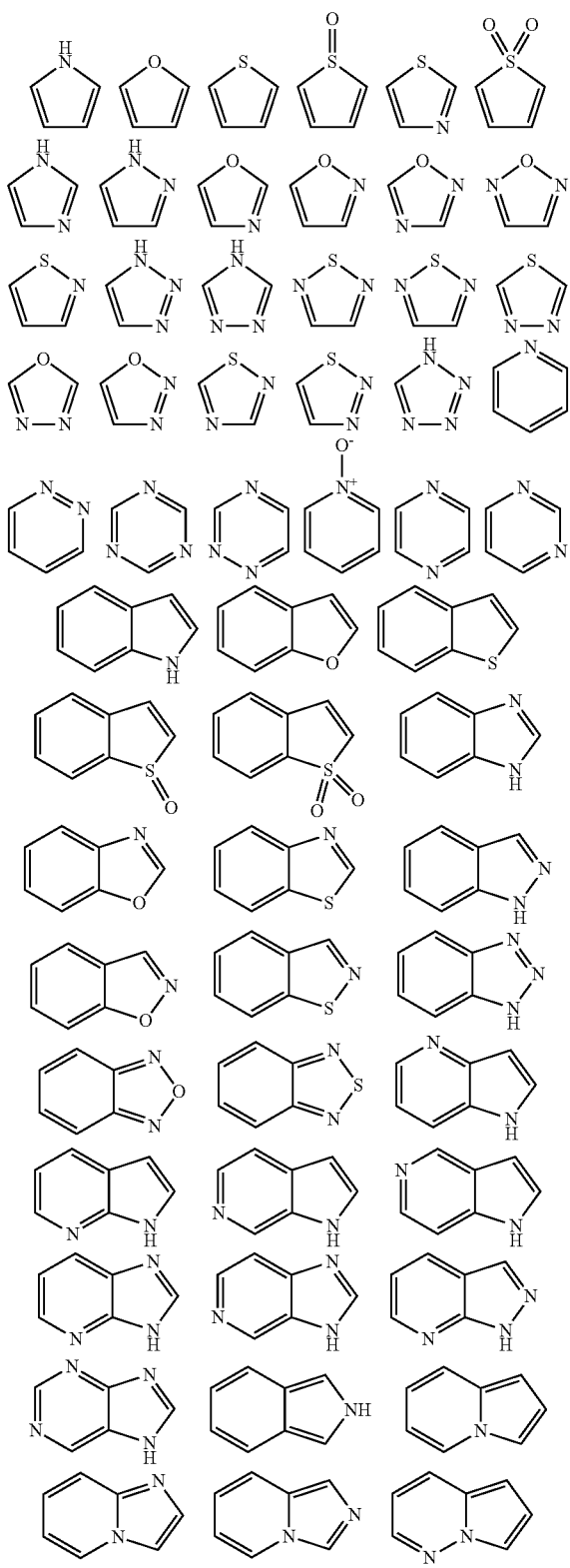

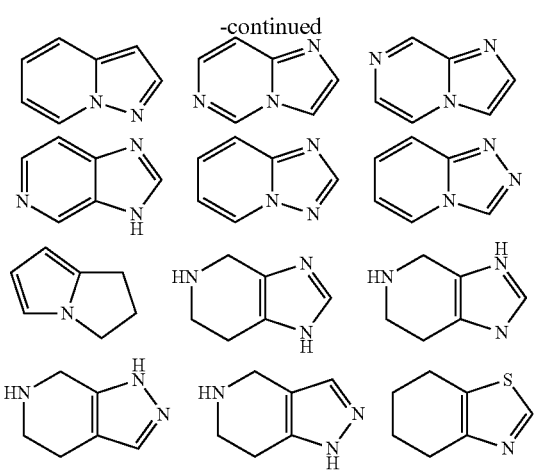

The above definition of heteroaryl also applies when heteroaryl is part of another group as in heteroarylamino or heteroaryloxy, for example.

If the free valency of a heteroaryl is saturated, a heteroaromatic group is obtained.

The term heteroarylene can therefore be derived from the previously defined heteroaryl. Heteroarylene, unlike heteroaryl, is bivalent and requires two binding partners. Formally, the second valency is obtained by removing a hydrogen atom from a heteroaryl. Corresponding groups are for example pyrrolyl and

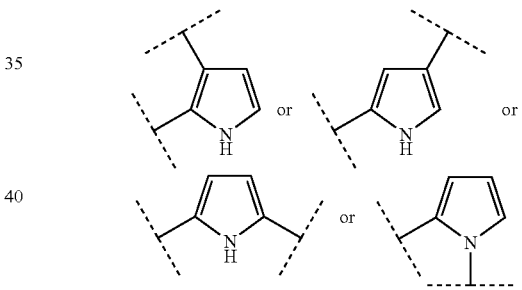

etc.

The above definition of heteroarylene also applies when heteroarylene is part of another group as in HO-heteroaryleneamino or $H_2N$-heteroaryleneoxy, for example.

The bivalent groups mentioned above (alkylene, alkenylene, alkynylene etc.) may also be part of composite groups (e.g. $H_2N$—$C_{1-4}$alkylene- or HO—$C_{1-4}$alkylene-). In this case one of the valencies is saturated by the attached group (here: —$NH_2$, —OH), so that a composite group of this kind written in this way is only a monovalent substituent over all.

By substituted is meant that a hydrogen atom which is bound directly to the atom under consideration, is replaced by another atom or another group of atoms (substituent). Depending on the starting conditions (number of hydrogen atoms) mono- or polysubstitution may take place on one atom. Substitution with a particular substituent is only possible if the permitted valencies of the substituent and of the atom that is to be substituted correspond to one another and the substitution leads to a stable compound (i.e. to a compound which is not converted spontaneously, e.g. by rearrangement, cyclisation or elimination).

Bivalent substituents such as =S, =NR, =NOR, =NNRR, =NN(R)C(O)NRR, =N₂ or the like, may only be substituted at carbon atoms, wherein the bivalent substituent =O may also be a substituent at sulphur. Generally, substitution may be carried out by a bivalent substituent only at ring systems and requires replacement by two geminal hydrogen atoms, i.e. hydrogen atoms that are bound to the same carbon atom that is saturated prior to the substitution. Substitution by a bivalent substituent is therefore only possible at the group —CH₂— or sulphur atoms of a ring system.

Stereochemistry/Solvates/Hydrates: Unless stated otherwise a structural formula given in the description or in the claims or a chemical name refers to the corresponding compound itself, but also encompasses the tautomers, stereoisomers, optical and geometric isomers (e.g. enantiomers, diastereomers, E/Z isomers, etc.), racemates, mixtures of separate enantiomers in any desired combinations, mixtures of diastereomers, mixtures of the forms mentioned hereinbefore (if such forms exist) as well as salts, particularly pharmaceutically acceptable salts thereof. The compounds and salts according to the invention may be present in solvated form (e.g. with pharmaceutically acceptable solvents such as e.g. water, ethanol etc.) or in unsolvated form. Generally, for the purposes of the present invention the solvated forms, e.g. hydrates, are to be regarded as of equal value to the unsolvated forms.

Salts: The term "pharmaceutically acceptable" is used herein to denote compounds, materials, compositions and/or formulations which are suitable, according to generally recognised medical opinion, for use in conjunction with human and/or animal tissue and do not have or give rise to any excessive toxicity, irritation or immune response or lead to other problems or complications, i.e. correspond overall to an acceptable risk/benefit ratio.

The term "pharmaceutically acceptable salts" relates to derivatives of the chemical compounds disclosed in which the parent compound is modified by the addition of acid or base. Examples of pharmaceutically acceptable salts include (without being restricted thereto) salts of mineral or organic acids in relation to basic functional groups such as for example amines, alkali metal or organic salts of acid functional groups such as for example carboxylic acids, etc. These salts include in particular acetate, ascorbate, benzenesulphonate, benzoate, besylate, bicarbonate, bitartrate, bromide/hydrobromide, Ca-edetate/edetate, camsylate, carbonate, chloride/hydrochloride, citrate, edisylate, ethane disulphonate, estolate, esylate, fumarate, gluceptate, gluconate, glutamate, glycolate, glycollylarsnilate, hexylresorcinate, hydrabamine, hydroxymaleate, hydroxynaphthoate, iodide, isothionate, lactate, lactobionate, malate, maleate, mandelate, methanesulphonate, mesylate, methylbromide, methylnitrate, methylsulphate, mucate, napsylate, nitrate, oxalate, pamoate, pantothenate, phenyl acetate, phosphate/diphosphate, polygalacturonate, propionate, salicylate, stearate, subacetate, succinate, sulphamide, sulphate, tannate, tartrate, teoclate, toluenesulphonate, triethiodide, ammonium, benzathine, chloroprocaine, choline, diethanolamine, ethylenediamine, meglumin and procaine. Other pharmaceutically acceptable salts may be formed with cations of metals such as aluminium, calcium, lithium, magnesium, potassium, sodium, zinc, etc. (cf. also Pharmaceutical salts, Birge, S. M. et al., J. Pharm. Sci., (1977), 66, 1-19).

The pharmaceutically acceptable salts of the present invention may be prepared starting from the parent compound which carries a basic or acidic functionality, by conventional chemical methods. Generally, such salts may be synthesised by reacting the free acid or base form of these compounds with a sufficient amount of the corresponding base or acid in water or an organic solvent such as for example ether, ethyl acetate, ethanol, isopropanol, acetonitrile (or mixtures thereof). Salts of acids other than those mentioned above, which are useful for example for to purifying or isolating the compounds from the reaction mixtures (e.g. trifluoroacetates), are also to be regarded as part of the invention.

In a representation such as for example

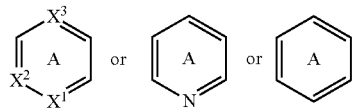

the letter A has the function of a ring designation in order to make it easier, for example, to indicate the attachment of the ring in question to other rings.

For bivalent groups in which it is crucial to determine which adjacent groups they bind and with which valency, the corresponding binding partners are indicated in brackets, where necessary for clarification purposes, as in the following representations:

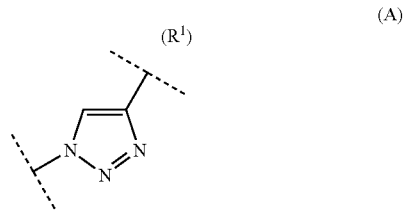

(A)

or (R²)—C(O)NH— or (R²)—NHC(O)—; Groups or substituents are frequently selected from among a number of alternative groups/substituents with a corresponding group designation (e.g. $R^a$, $R^b$ etc). If such a group is used repeatedly to define a compound according to the invention in different molecular parts, it must always be borne in mind that the various uses are to be regarded as totally independent of one another.

By a therapeutically effective amount for the purposes of this invention is meant a quantity of substance that is capable of obviating symptoms of illness or of preventing or alleviating these symptoms, or which prolong the survival of a treated patient.

List of Abbreviations

| | |
|---|---|
| ACN, CH₃CN | acetonitrile |
| Boc | tert.butoxy carbonyl |
| DCM | dichloromethane |
| DIPEA | diisopropylethyl amine |
| DMAP | dimethyl-pyridin-4-yl-amine |
| DMF | N,N-dimethylformamide |
| DMSO | dimethylsulphoxide |
| EDTA | ethylenediaminetetraacetic acid |
| EtOAc or EA | ethyl acetate |
| FCS | Fetal calf serum |
| h | hour(s) |
| HATU | N-[(dimethylamino)-(1H-1,2,3-triazolo[4,5-b]pyridin-1-yl)-methylene]-N-methylmethan-aminium hexafluorophosphate N-oxide |
| HPLC | high performance liquid chromatography |
| KOAc | potassium acetate |
| LiHMDS | lithium hexamethyl disilazide |
| M | Molar |

| | |
|---|---|
| Min | minute(s) |
| mL | Millilitre |
| MS | mass spectrometry |
| N | Normal |
| NMR | nuclear resonance spectroscopy |
| PE | petrol ether |
| PPh3 | triphenylphosphine |
| DIBAL | diisobutylaluminium hydride |
| RP | reversed phase |
| Rpm | rounds per minute |
| RT or rt | room temperature |
| TBME | tert.butyl methyl ether |
| TEA | triethylamine |
| tert | tertiary |
| TFA | trifluoroacetic acid |
| THF | tetrahydrofuran |
| $t_{Ret}$ | retention time [min] |
| TRIS | tris(hydroxymethyl)aminomethane |
| wt | wild type |
| wt % | weight percent |
| sat. | Saturated |
| nBuLi | n-butyllithium |

Other features and advantages of the present invention will become apparent from the following more detailed Examples which exemplary illustrate the principles of the invention without restricting its scope.

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds are named according to the Beilstein rules using the Autonom software (Beilstein). If a compound is to be represented both by a structural formula and by its nomenclature, in the event of a conflict the structural formula is decisive.

Chromatography

Thin layer chromatography is carried out on ready-made TLC plates of silica gel 60 on glass (with fluorescence indicator F-254) made by Merck.

The preparative high pressure chromatography (HPLC) of the example to compounds according to the invention is carried out with columns made by Waters (names: Sunfire C18, 5 μm, 30×100 mm Part. No. 186002572; X-Bridge C18, 5 μm, 30×100 mm Part. No. 186002982). The compounds are eluted using either different gradients of H$_2$O/ACN or H$_2$O/MeOH, wherein 0.1% HCOOH is added to the water (acid conditions). For chromatography under basic conditions H$_2$O/ACN gradients are also used, and the water is made basic according to the following recipe: 5 mL of ammonium hydrogen carbonate solution (158 g to 1 L H$_2$O) and 2 mL ammonia (7M in MeOH) are made up to 1 L with H$_2$O.

The normal-phase preparative high pressure chromatography (HPLC) of the example compounds according to the invention is carried out with columns made by Macherey & Nagel (name: Nucleosil, 50-7, 40×250 mm) and VDSoptilab (name: Kromasil 100 NH$_2$, 10 μM, 50×250 mm) The compounds are eluted using different gradients of DCM/MeOH with 0.1% NH$_3$ added to the MeOH.

The analytical HPLC (reaction monitoring) of intermediate compounds is carried out with columns made by Agilent, Waters and Phenomenex. The analytical equipment is also provided with a mass detector in each case.

HPLC Mass Spectroscopy/UV Spectrometry

The retention times/MS-ESI$^+$ for characterising the example compounds according to the invention are produced using an HPLC-MS apparatus (high performance liquid chromatography with mass detector) made by Agilent. Compounds that elute at the injection peak are given the retention time $t_{Ret}$=0.

HPLC-Methods

Preparative

Prep. HPLC1

| | |
|---|---|
| HPLC: | 333 and 334 Pumps |
| Column: | Waters X-Bridge C18, 5 μm, 30 × 100 mm, Part. No. 186002982 |
| Eluent: | A: 10 mM NH$_4$HCO$_3$ in H$_2$O; B: Acetonitril (HPLC grade) |
| Detection: | UV/Vis-155 |
| Flow: | 50 mL/min |
| Gradient: | 0.00 min: 5 % B |
| | 3.00-15.00 min: variable |
| | 15.00-17.00 min: 100 % B |

Prep. HPLC2

| | |
|---|---|
| HPLC: | 333 and 334 Pumps |
| Column: | Waters Sunfire C18, 5 μm, 30 × 100 mm, Part. No. 186002572 |
| Eluent: | A: H$_2$O + 0.2% HCOOH; |
| | B: Acetonitril (HPLC grade) + 0.2% HCOOH |
| Detection: | UV/Vis-155 |
| Flow: | 50 mL/min |
| Gradient: | 0.00 min: 5% B |
| | 3.00-15.00 min: variable |
| | 15.00-17.00 min: 100% B |

Analytical Method

AM1

| | |
|---|---|
| HPLC: | Agilent 1100 Series |
| MS: | Agilent LC/MSD SL |
| Column: | Waters, XBridge ™ C18, 2.5 μm, 2.1 × 20 mm Part. No. 186003201 |
| Eluant | A: 0.1% NH$_3$ (=pH 9-10); B: ACN HPLC grade |
| Detection: | MS: Positive and negative |
| Mass range: | 120-800 m/z |
| Flow: | 1.00 mL/min |
| Column temperature: | 60° C. |
| Injection: | 5 μL |
| Gradient: | 0.00 min 5% B |
| | 0.00-2.50 min 5% -> 95% B |
| | 2.50-2.80 min 95% B |
| | 2.81-3.10 min 95% -> 5% B |

AM2

| | |
|---|---|
| HPLC: | Agilent 1200 |
| Column: | Venusil XBP-C18 2.1 × 50 mm, 5 u m+ |
| Eluan: | A: 4L H$_2$O (with 1.5 ml TFA); |
| | B: 4L Acetonitrile (with 0.75 ml TFA) |
| Flow rate: | 1.0 ml/min |
| Wave length: | 220 nm |
| Column Temp: | 50° C. |

| Gradient: | |
|---|---|
| Time(min) | B % |
| 0.00 | 10 |
| 4.00 | 80 |
| 6.00 | 80 |
| 6.01 | 10 |

AM3

| | |
|---|---|
| HPLC: | Agilent 1200 |
| Column: | Venusil XBP-C18 2.1 × 50 mm, 5 u m |
| Mobile Phase: | A: 4L H$_2$O (with 1.5 ml TFA); |
| | B: 4L Acetonitrile (with 0.75 ml TFA) |
| Flow rate: | 1.0 ml/min |
| Wave length: | 220 nm |
| Column Temp: | 50° C. |

Gradient:

| Time(min) | B % |
|---|---|
| 0.00 | 30 |
| 2.00 | 90 |
| 2.48 | 90 |
| 2.50 | 30 |
| 3.00 | 30 |

AM4

| | |
|---|---|
| HPLC: | Agilent1200HPLC, 6110MSD |
| Column: | Xbridge C18 2.1 × 50 mm, 5 u m |
| Mobile Phase: | A: H$_2$O (10 mmol/L NH$_4$HCO$_3$); |
| | B: Acetonitrile |
| Flow rate: | 1.0 ml/min |
| Wave length: | 220 nm |
| Column Temp: | 50° C. |

Gradient:

| Time(min) | B % |
|---|---|
| 0.00 | 10 |
| 2.00 | 80 |
| 2.48 | 80 |
| 2.50 | 10 |
| 3.00 | 10 |

AM5

| | |
|---|---|
| HPLC: | Agilent 1200, 6110MS |
| Column: | Venusil XBP-C18 2.1 × 50 mm, 5 u m |
| Mobile Phase: | A: 4L H$_2$O (with 1.5 ml TFA); |
| | B: 4L Acetonitrile (with 0.75 ml TFA) |

Gradient:

| Time(min) | B % |
|---|---|
| 0.00 | 10 |
| 0.40 | 10 |
| 3.40 | 100 |
| 3.85 | 100 |
| 3.86 | 10 |

| | |
|---|---|
| Flow rate: | 0.8 ml/min |
| Wave length: | 220 nm |
| Column Temp: | 50° C. |

AM6

| | |
|---|---|
| HPLC: | Agilent 1200, 6120MSD |
| Column: | Venusil XBP-C18 2.1 × 50 mm, 5 u m |
| Mobile Phase: | A: 4L H$_2$O (with 1.5 ml TFA); |
| | B: 4L Acetonitrile (with 0.75 ml TFA) |
| Flow rate: | 0.8 ml/min |
| Wave length: | 220 nm |
| Column Temp: | 50° C. |

Gradient:

| Time(min) | B % |
|---|---|
| 0.00 | 1 |
| 0.40 | 1 |
| 3.40 | 90 |
| 3.85 | 100 |
| 3.86 | 1 |

AM7

| | |
|---|---|
| HPLC: | Agilent 1200 |
| Column: | Venusil XBP-C18 2.1 × 50 mm, 5 u m |
| Mobile Phase: | A: 4L H$_2$O (with 1.5 ml TFA); |
| | B: 4L Acetonitrile (with 0.75 ml TFA) |
| Flow rate: | 0.8 ml/min |
| Wave length: | 220 nm |
| Column Temp: | 50° C. |

Gradient:

| Time(min) | B % |
|---|---|
| 0.00 | 25 |
| 0.40 | 25 |
| 3.40 | 100 |
| 3.85 | 100 |
| 3.86 | 25 |
| 4.50 | 25 |

AM8

| | |
|---|---|
| HPLC: | Agilent 1100/1200 Series |
| MS: | Agilent 1100 LC/MSD SL |
| Column: | Waters Sunfire, 5.0 μm, 2.1 × 50 mm |
| Eluent: | A: H$_2$O + 0.2% HCOOH; B: CH$_3$CN |
| Detection:: | ESI |
| Mass range: | 100-1200 m/z |
| Flow: | 1.20 mL/min |
| Column temp: | 35° C. |
| Gradient: | 0.01 min: 5% B |
| | 0.01-1.50 min: 5% → 95% B |
| | 1.50-2.00 min: 100% B |

AM9

| | |
|---|---|
| HPLC: | Agilent 1100/1200 Series |
| MS: | Agilent 1100 LC/MSD SL |
| Column: | WatersXBridge C18 2.1 × 50 mm, 5.0 μ |
| Gradient: | 95:5 Water (5 mM NH$_4$HCO$_3$, 19 mM NH$_3$): CH$_3$CN in 1.24 min from 5:95, 0.75 min isocratic to 5:95 |
| Flow: | 1.2 mL/min |

AM10

| | |
|---|---|
| HPLC: | Agilent 1100 Series |
| MS: | Agilent LC/MSD G6140 A |
| Column: | Agilent Poroshell SB C18, 2.7 μm, 2.1 × 30 mm |
| Eluent: | A: 0.11% formic acid in H$_2$O; |
| | B: 0.1% formic acid in CH$_3$CN |
| Detection: | MS: Positive mode |
| Mass range: | 150-700 m/z |
| Flow: | 1.40 mL/min |
| Column temp: | 45° C. |

-continued

| Gradient: | 0.00 min: | 15% B |
| --- | --- | --- |
|  | 0.00-1.00 min: | 15% → 95% B |
|  | 1.00-1.13 min: | 95% B |
| Stop time: | 1.23 min | |

AM11

| HPLC: | Agilent 1100/1200 Series |
| --- | --- |
| MS: | Agilent LC/MSD SL |
| Column: | Waters X-Bridge C18 OBD, 5 μm, 2.1 × 50 mm |
| Eluent: | A: 5 mM $NH_4HCO_3$/19 mM $NH_3$ in $H_2O$; B: $CH_3CN$ |
| Detection: | MS: Multimode ESI Positive and negative mode |
| Mass range: | 105-1200 m/z |
| Flow: | 1.20 ml/min |
| Column temp: | 35° C. |
| Gradient: | 0.00-1.25 min: 5% → 100% B |
|  | 1.25-2.00 min: 100% B |
|  | 2.00-2.01 min: 100% → 5% B |

AM12

| HPLC: | Agilent 1200 |
| --- | --- |
| MS: | Agilent LC/MSD SL |
| Column: | Venusil XBP-C18 2.1 × 50 mm, 5 μm |
| Eluent: | A: 4L $H_2O$ (with 1.5 ml TFA); |
|  | B: 4L $CH_3CN$ (with 0.75 ml TFA) |
| Flow rate: | 1.0 ml/min |
| Column temp: | 50° C. |
| Gradient: | 0.00 min 10% B |
|  | 2.00 min 80% B |
|  | 2.48 min 80% B |
|  | 2.50 min 10% B |
|  | 3.00 min 10% B |

EXAMPLE 1

Preparation of 6-(3,5-Dimethyl-isoxazol-4-yl)-3-methyl-4-phenyl-3,4-dihydro-1H-quinazolin-2-one

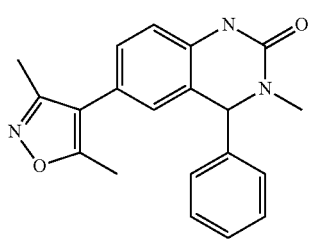 [SMILES: Cc1noc(C)c1-c1ccc2c(c1)C(c1ccccc1)N(C)C(=O)N2]

Reaction scheme:

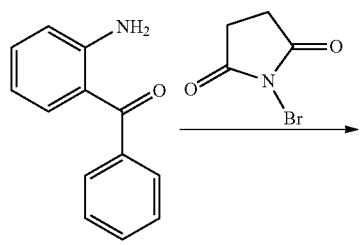

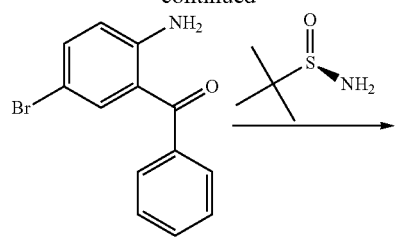

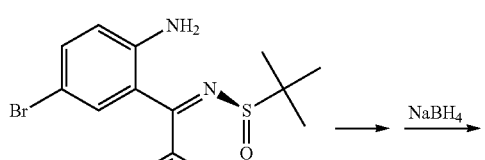

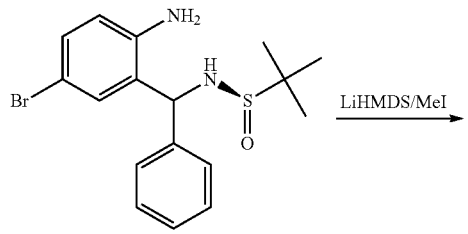

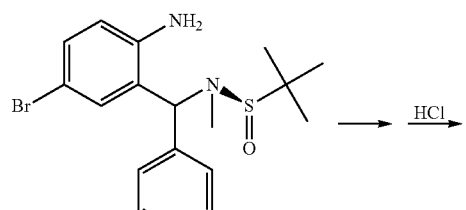

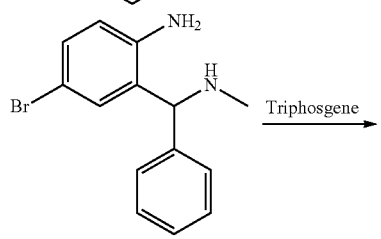

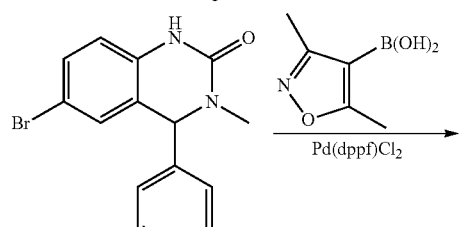

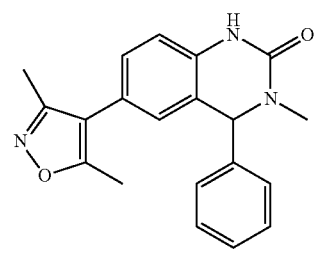 [SMILES: Cc1noc(C)c1-c1ccc2c(c1)C(c1ccccc1)N(C)C(=O)N2]

25

(2-Amino-5-bromo-phenyl)-phenyl-methanone

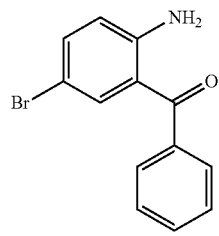

To a solution of (2-Amino-phenyl)-phenyl-methanone (5 g, 25 mmol) in DCM (100 mL) is cooled to −10° C., then NBS (4.512 g, 25 mmol) is added in 30 minutes. After the addition the mixture is stirred at −10° C. for 2 h. The mixture is diluted with DCM, washed with salt NaHCO$_3$ (2×100 mL), salt NaCl (100 mL), dried over anhydrous Na$_2$SO$_4$, filtered and concentrated to give product (6.3 g), which is used for the next step without further purification.

TLC (10:1, petrol ether/ethyl acetate) Rf=0.6

2-Methyl-propane-2-sulfinic acid (2-amino-5-bromo-phenyl)-phenyl-methyleneamide

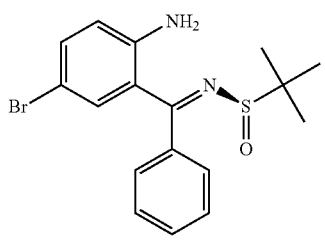 [SMILES: CC(C)(C)[S@@](=O)/N=C(\c1ccccc1)c1cc(Br)ccc1N]

A solution of (2-Amino-5-bromo-phenyl)-phenyl-methanone (67 g, 244 mmol), 2-Methyl-propane-2-sulfinic acid amide (35.38 g, 292 mmol) and Ti(OEt)$_4$ (111.15 g, 487 mmol) in THF (800 mL) is heated to reflux overnight. Then H$_2$O is added and filtered and concentrated. The residue is purified by chromatography on silica gel to give desired product.

Yield: 70 g (76%)

TLC (10:1, petrol ether/ethyl acetate) Rf=0.3

2-Methyl-propane-2-sulfinic acid [(2-amino-5-bromo-phenyl)-phenyl-methyl]-amide

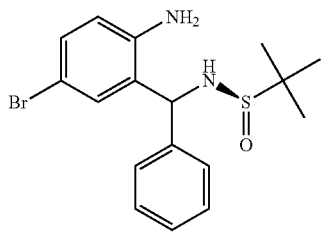 [SMILES: CC(C)(C)[S@@](=O)NC(c1ccccc1)c1cc(Br)ccc1N]

2-Methyl-propane-2-sulfinic acid (2-amino-5-bromo-phenyl)-phenyl-methyleneamide (70 g, 184 mol) is dissolved in 98:2 THF/H$_2$O (800 mL) and was cooled to −50° C. Then NaBH$_4$ (17.5 g, 462 mol) is added and the mixture is stirred at room temperature overnight. Then H$_2$O is added and concentrated and extracted with EtOAc. The organic layer is concentrated to give product.

Yield: 60 g (86%)

TLC (1:1, petrol ether/ethyl acetate) Rf=0.5

26

2-Methyl-propane-2-sulfinic acid [(2-amino-5-bromo-phenyl)-phenyl-methyl]-methyl-amide

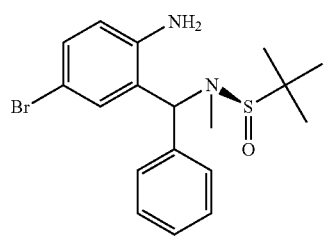 [SMILES: CN(C(c1ccccc1)c1cc(Br)ccc1N)[S@](=O)C(C)(C)C]

To a solution of 2-Methyl-propane-2-sulfinic acid [(2-amino-5-bromo-phenyl)-phenyl-methyl]-amide (60 g, 157 mmol) in DMF (700 mL) is cooled to −20° C., then LiHMDS (163 mL, 173 mmol) is added dropwise. After the addition the mixture is stirred at −20° C. for 1 h. Then CH$_3$I (22.3 g, 157 mmol) is added dropwise. After the addition the mixture is warm to r.t. for 2 h. Then H$_2$O is added and is was extracted with MeO(CH$_3$)$_3$, dried over Na$_2$SO$_4$ and concentrated to give product.

Yield: 60 g (96%)

TLC (1:1, petrol ether/ethyl acetate) Rf=0.5

4-Bromo-2-(methylamino-phenyl-methyl)-phenylamine

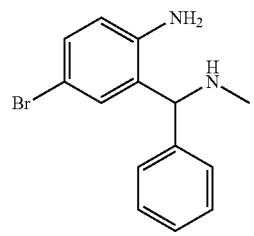 [SMILES: CNC(c1ccccc1)c1cc(Br)ccc1N]

To a solution of 2-Methyl-propane-2-sulfinic acid [(2-amino-5-bromo-phenyl)-phenyl-methyl]-methyl-amide (60 g, 152 mmol) in EtOAc/HCl (600 mL) is stirred at r.t. for 2 h. The mixture is concentrated and NaHCO$_3$ is added to brought the PH>7, extracted with EtOAc. The organic layer is concentrated to give product. This is used in the next step without further purification.

Yield: 40 g (90.5%)

TLC (1:1, petrol ether/ethyl acetate) Rf=0.3

6-Bromo-3-methyl-4-phenyl-3,4-dihydro-1H-quinazolin-2-one

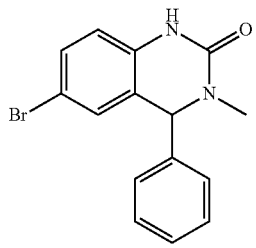

A solution of reactant 4-Bromo-2-(methylamino-phenyl-methyl)-phenylamine (3.4 g, 12 mmol) in THF (150 mL) is added triphosgene (3.81 g, 13 mmol). After the addition the mixture is stirred at r.t. for 3 h. Then H$_2$O is added and is extacd with EtOAc, dried over Na$_2$SO$_4$ and concentrated. The residue is purified by chromatography on silica gel to give product.

Yield: 1.85 g (50%)
TLC (1:1, petrol ether/ethyl acetate) Rf=0.3
HPLC-MS: M+H=317/319; $t_{Ret}$=2.87 min; AM5

6-(3,5-Dimethyl-isoxazol-4-yl)-3-methyl-4-phenyl-3,4-dihydro-1H-quinazolin-2-one

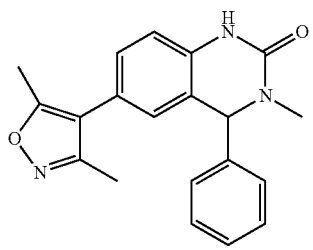

A solution of 6-Bromo-3-methyl-4-phenyl-3,4-dihydro-1H-quinazolin-2-one (15 g, 50.44 mmol) in dioxane (200 mL) is added NaCO$_3$ (5.03 g, 474 mmol) and 3,5-dimethyl-isoxazole-4-boronic acid (7.8 g, 55.498 mmol) and Pd(dppf)Cl$_2$ (4.268 g, 5.044 mmol) then the mixture is refluxed at 100° C. overnight in dioxane (200 mL). The reaction is concentrated and was purified by chromatography on silica gel to give product.

Yield: 1.5 g (9%)
HPLC-MS: M+H=334; $t_{Ret}$=2.70 min; AM5

EXAMPLE 2

Preparation of (S) 6-(3,5-Dimethyl-isoxazol-4-yl)-3-methyl-4-phenyl-3,4-dihydro-1H-quinazolin-2-one

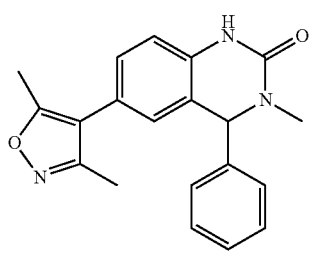

Preparative Separation Method
HPLC: Thar 350 preparative SFC
Column: ChiralPak AY-20 um, 300×50 mmI.D.
Mobile phase: A for CO$_2$ and B for EtOH
Gradient: B 40%
Flow rate: 220 mL/min
Back pressure: 100 bar
Column temperature: 38° C.
Wavelength: 220 nm
Cycle time: ~4.8 min
Sample preparation: Compound of example 1 is dissolved in methanol to ~30 mg/ml
Injection: 16 ml per injection.

After separation, the fractions are concentrated in vacuo at 40° C. to obtain the desired isomers.

EXAMPLE 3

Preparation of 6-(3,5-Dimethyl-isoxazol-4-yl)-1,3-dimethyl-4-phenyl-3,4-dihydro-1H-quinazolin-2-one

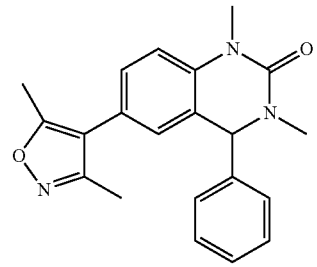 [SMILES: Cc1noc(C)c1-c1ccc2c(c1)C(c1ccccc1)N(C)C(=O)N2C]

6-Bromo-1,3-dimethyl-4-phenyl-3,4-dihydro-1H-quinazolin-2-one

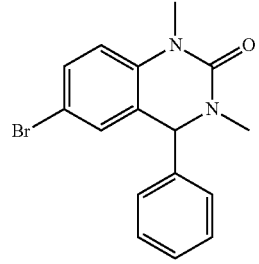 [SMILES: CN1C(=O)N(C)C(c2ccccc2)c2cc(Br)ccc21]

A mixture of 6-Bromo-3-methyl-4-phenyl-3,4-dihydro-1H-quinazolin-2-one (0.2 g, 0.6 mmol) in DMF (10 mL) is cooled to 0° C., then NaH (16.7 mg, 0.7 mmol) is added. After the addition the mixture is stirred at 0° C. for 0.5 h. Then CH$_3$I (107 mg, 0.76 mmol) is added and the mixture is stirred at r.t. for 2 h. Then H$_2$O is added and is extracted with EtOAc, dried over Na$_2$SO$_4$ and concentrated to give product. This is used in the next step without further purification.

Yield: 100 mg (47.9%)
TLC (1:1, petrol ether/ethyl acetate) Rf=0.5

6-(3,5-Dimethyl-isoxazol-4-yl)-1,3-dimethyl-4-phenyl-3,4-dihydro-1H-quinazolin-2-one

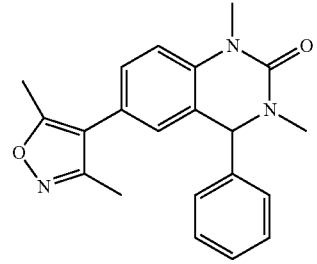 [SMILES: Cc1noc(C)c1-c1ccc2c(c1)C(c1ccccc1)N(C)C(=O)N2C]

A solution of 6-Bromo-1,3-dimethyl-4-phenyl-3,4-dihydro-1H-quinazolin-2-one (100 mg, 0.3 mmol) in dioxane (3 mL) is added NaCO$_3$ (50 mg, 0.45 mmol) and 3,5-dimethyl-isoxazole-4-boronic acid (56 mg, 0.39 mmol) and Pd(dppf)Cl$_2$ then the mixture is refluxed at 100° C. overnight. The reaction is concentrated and is purified by chromatography on silica gel to give product.

Yield: 5 mg (5%)
HPLC-MS: M+H=348; $t_{Ret}$=3.26 min; AM6

EXAMPLE 4

Preparation of 6-(3,5-Dimethyl-isoxazol-4-yl)-3-(1-methyl-piperidin-4-ylmethyl)-4-phenyl-3,4-dihydro-1H-quinazolin-2-one

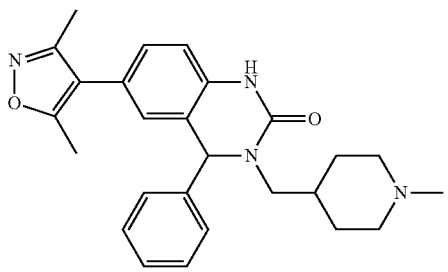 [SMILES: Cc1noc(C)c1-c1ccc2c(c1)C(c1ccccc1)N(CC1CCN(C)CC1)C(=O)N2]

Reaction scheme:

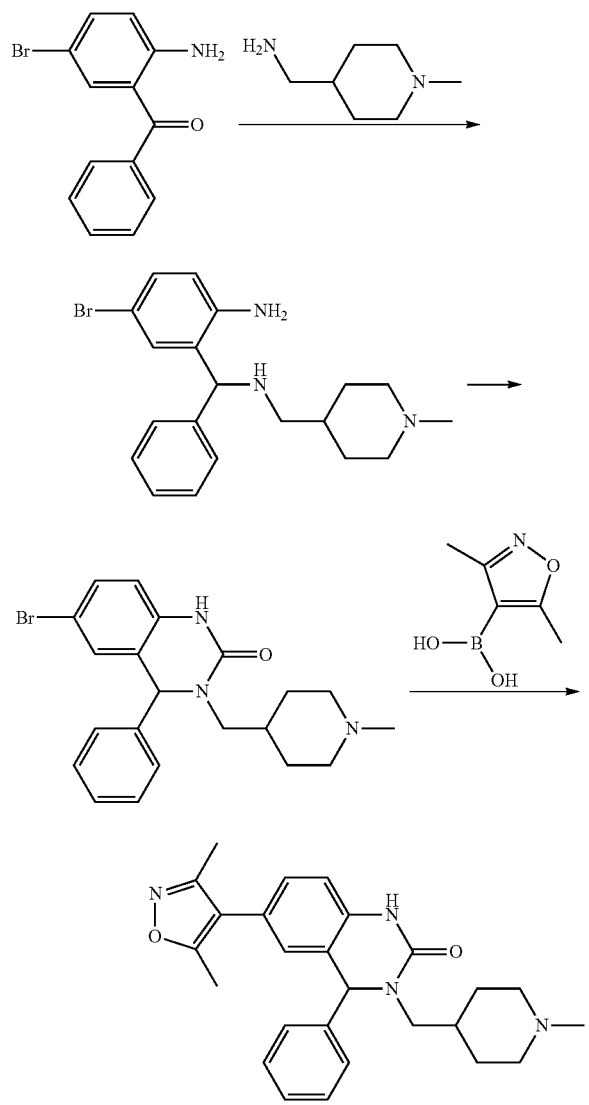

4-Bromo-2-[[(1-methyl-4-piperidyl)methylamino]-phenyl-methyl]aniline

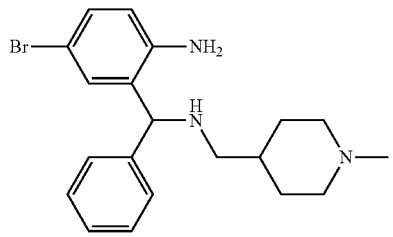 [SMILES: CN1CCC(CNC(c2ccccc2)c2cc(Br)ccc2N)CC1]

A mixture of (2-Amino-5-bromo-phenyl)-phenyl-methanone (1 g, 3.6 mmol), 1-Methyl-4-methylaminopiperidine (0.46 g, 3.6 mmol) and Ti(OEt)$_4$ (1.65 g, 7.2 mmol) in THF (30 ml) is stirred at 66° C. over night. The mixture is cooled to rt, poured onto an ice-water-mixture and extracted with EtOAc. The combined organic layers are dried over MgSO$_4$ and concentrated in vacuo. EtOH (10 ml) and sodium borohydride (0.57 g, 15.1 mmol) is added and the mixture stirred at rt for 72 h. Water is added and the mixture is extracted with EtOAc. The combined organic layers are dried over MgSO$_4$ and concentrated in vacuo. The product is used without further purification.

Yield: 1.05 g (75%)
HPLC-MS: M+H=388/390; $t_{Ret}$=1.79 min; AM11

6-Bromo-3-[(1-methyl-4-piperidyl)methyl]-4-phenyl-1,4-dihydroquinazolin-2-one

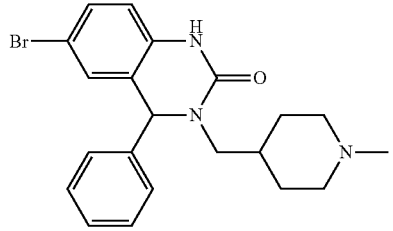 [SMILES: CN1CCC(CN2C(=O)Nc3ccc(Br)cc3C2c2ccccc2)CC1]

A mixture of 4-Bromo-2-[[(1-methyl-4-piperidyl)-methylamino]-phenyl-methyl]aniline (0.96 g, 2.5 mmol), N,N'-carbonyldiimidazole (0.4 g, 2.5 mmol) and THF (20 ml) is stirred overnight at 60° C. Water is added and the mixture is extracted with EtOAc. The combined organic layers are dried over MgSO$_4$ and concentrated in vacuo. The product is purified by RP HPLC.

Yield: 0.4 g (42%)
HPLC-MS: M+H=414/416; $t_{Ret}$=1.69 min; AM11

6-(3,5-Dimethylisoxazol-4-yl)-3-[(1-methyl-4-piperidyl)methyl]-4-phenyl-1,4-dihydroquinazolin-2-one

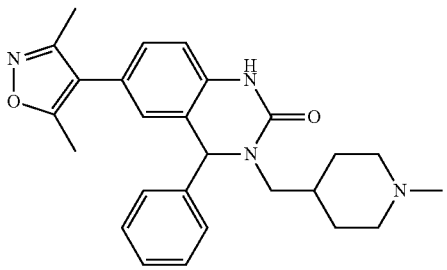 [SMILES: Cc1noc(C)c1-c1ccc2c(c1)C(c1ccccc1)N(CC1CCN(C)CC1)C(=O)N2]

To a mixture of 6-Bromo-3-[(1-methyl-4-piperidyl)methyl]-4-phenyl-1,4-dihydroquinazolin-2-one (100 mg, 0.24 mmol), 3,5-dimethylisoxazole-4-boronic acid (51 mg, 0.36 mmol), Na$_2$CO$_3$ (77 mg, 0.73 mmol) in dioxane (1.6 ml) with MeOH (0.4 ml) and water (0.2 ml) 1,1'-Bis(diphenylphosphino)ferrocene]dichloro-palladium(II) (17 mg, 0.02 mmol) is added. The mixture is stirred for 5 h at 80° C., concentrated in vacuo and the product purified by RP HPLC.

Yield: 0.09 g (85%)

HPLC-MS: M+H=431; $t_{Ret}$=1.08 min; AM1

The following examples are prepared analogously:

EXAMPLE 5

6-(3,5-Dimethylisoxazol-4-yl)-4-phenyl-3-(tetrahydropyran-4-ylmethyl)-1,4-dihydroquinazolin-2-one

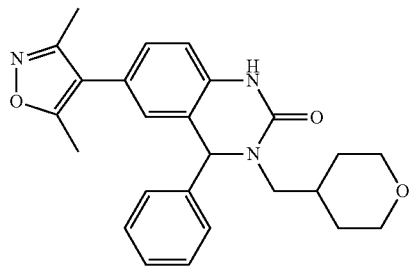 [SMILES: Cc1noc(C)c1-c1ccc2c(c1)C(c1ccccc1)N(CC1CCOCC1)C(=O)N2]

HPLC-MS: M+H=418; $t_{Ret}$=1.13 min; AM1

EXAMPLE 6

3-Benzyl-6-(3,5-dimethylisoxazol-4-yl)-4-phenyl-1,4-dihydroquinazolin-2-one

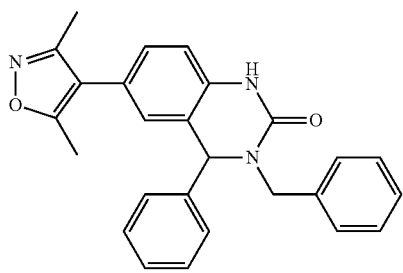 [SMILES: Cc1noc(C)c1-c1ccc2c(c1)C(c1ccccc1)N(Cc1ccccc1)C(=O)N2]

HPLC-MS: M+H=410; $t_{Ret}$=1.29 min; AM1

EXAMPLE 7

Preparation of 4-(4-Chloro-phenyl)-6-(3,5-dimethylisoxazol-4-yl)-3-methyl-3,4-dihydro-1H-quinazolin-2-one

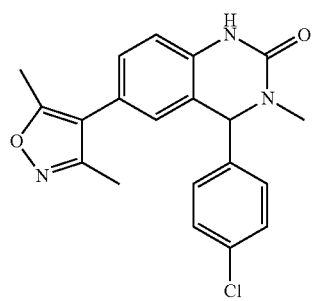

Reaction scheme

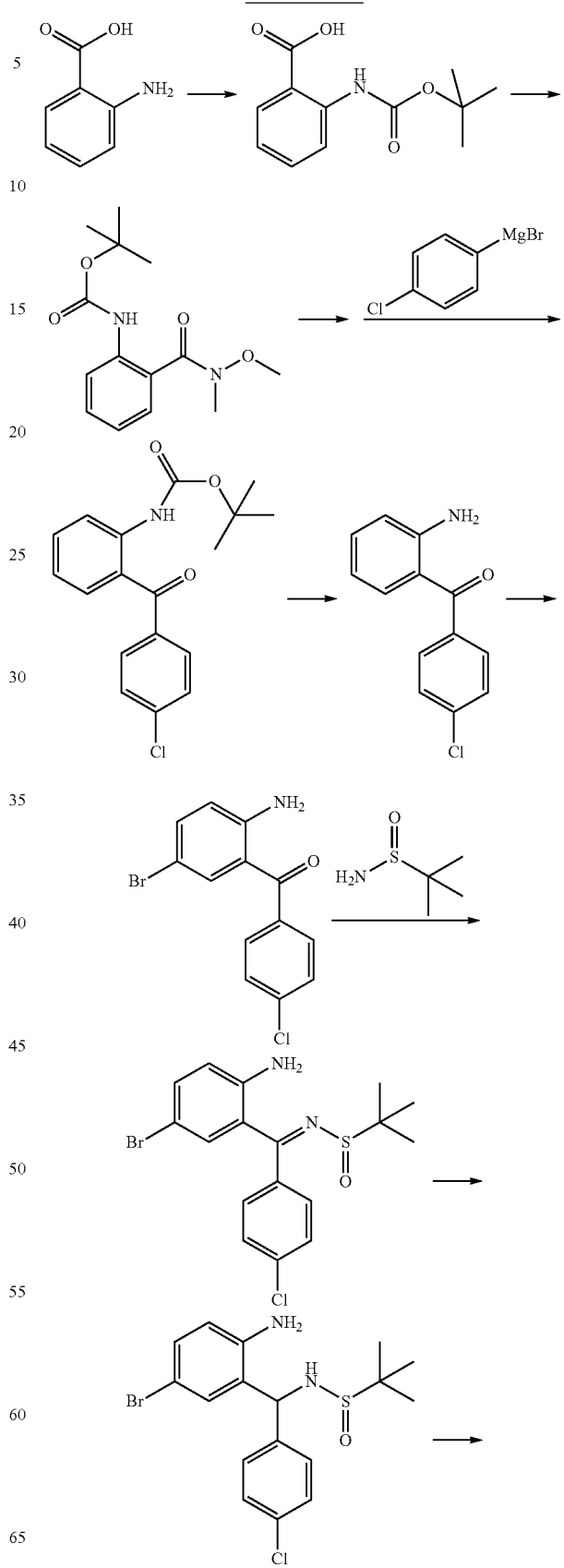

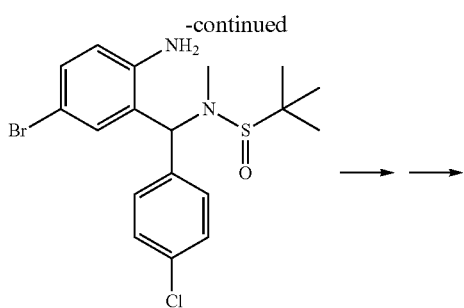

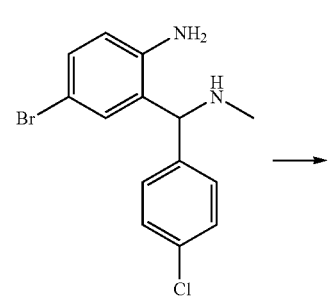

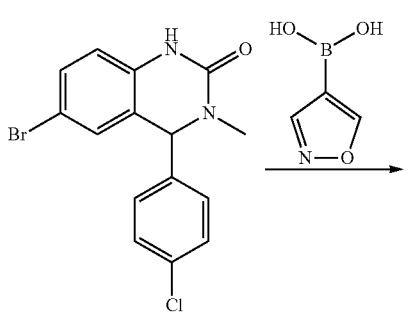

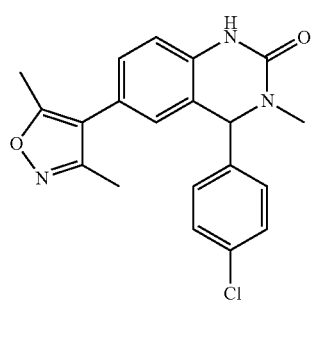 [SMILES: Cc1noc(C)c1-c1ccc2c(c1)C(c1ccc(Cl)cc1)N(C)C(=O)N2]

2-tert-Butoxycarbonylamino-benzoic acid

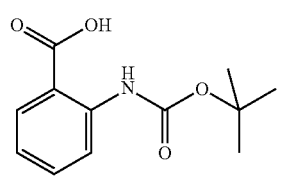 [SMILES: CC(C)(C)OC(=O)Nc1ccccc1C(=O)O]

A solution of 2-Amino-benzoic acid (20 g, 0.15 mol) in 1:1 THF/H₂O (290 ml) is adjusted to pH10 by addition of 2M NaOH. Boc₂O (35.0 g, 0.16 mol) is then added. The mixture is stirred at RT. The THF is removed in vacuo, then the mixture is adjusted to pH4 by addition of 15% citric acid. The mixture is filtered to provide the desired product. Yield: 22.0 g (63.6%).

[2-(Methoxy-methyl-carbamoyl)-phenyl]-carbamic acid tert-butyl ester

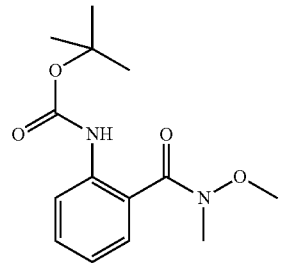 [SMILES: CON(C)C(=O)c1ccccc1NC(=O)OC(C)(C)C]

To the stirred solution of 2-tert-Butoxycarbonylamino-benzoic acid in acetonitrile (20 ml) is added N,O-hydroxylaminehydrochloride, EDC.HCl (1.520 g, 7.929 mmol), HOBT (1.300 g, 8.497 mmol) and triethylamine (2.500 g, 24.752 mmol) is stirred at room temperature for 40 mins. The progress of the reaction is monitored by TLC (30% EtOAc/Hexane).

After completion of the reaction, the reaction mixture is quenched with water and extracted with EtOAc (2×20 ml), the combined organic fractions are washed with brine (10 mL), dried over anhydrous Na₂SO₄ and concentrated in vacuo to afford a liquid. This is used in the next reaction without further purification.

Yield: 1.20 g (56.4%)

[2-(4-Chloro-benzoyl)-phenyl]-carbamic acid tert-butyl ester

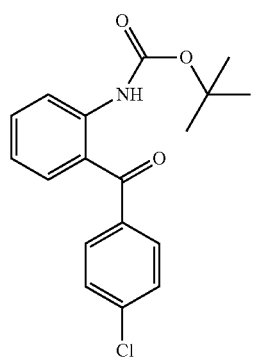 [SMILES: CC(C)(C)OC(=O)Nc1ccccc1C(=O)c1ccc(Cl)cc1]

To a solution of [2-(Methoxy-methyl-carbamoyl)-phenyl]-carbamic acid tert-butyl ester (15.0 g, 1.54 mmol) dissolved in THF (200 mL) is added p-chlorophenylmagnesium bromide (1.0M, 150 mL) at −30° C. The mixture is then stirred at RT overnight. The mixture is quenched with NH₄Cl, extracted with ethyl acetate, dried over NaSO₄ and concentrated then purified by silica gel. This provides the desired product.

Yield: 11.60 g (65%)

(2-Amino-phenyl)-(4-chloro-phenyl)-methanone

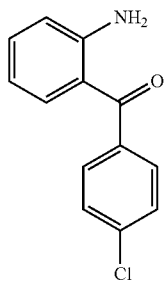 [SMILES: Nc1ccccc1C(=O)c1ccc(Cl)cc1]

To a solution of [2-(4-Chloro-benzoyl)-phenyl]-carbamic acid tert-butyl ester (11.6 g, 0.035 mol) dissolved in 200 mL HCl/ethyl acetate is stirred at RT. The ethyl acetate is removed in vacuo. The mixture is adjusted to pH10 by addition of aqueous NaOH. The mixture is extracted with ethyl acetate, dried over NaSO$_4$ and concentrated. This provides the desired compound. This is used without further purification.
Yield: 8.10 g (100%)

(2-Amino-5-bromo-phenyl)-(4-chloro-phenyl)-methanone

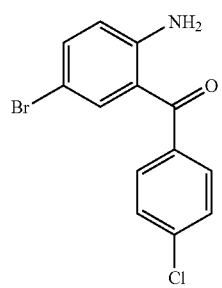

To a solution of (2-Amino-phenyl)-(4-chloro-phenyl)-methanone (9.41 g, 0.04 mmol) dissolved in 150 mL DCM was added NBS (7.25 g, 0.04mol) at 0° C. The mixture is stirred at RT for overnight. The mixture is extracted with DCM, washed with NaHCO$_3$, dried over NaSO$_4$ and concentrated. This provides the desired compound. This is used without further purification.
Yield: 11.60 g (92%)
HPLC-MS: M+H=310/312; t$_{Ret}$=1.72 min; AM3

2-Methyl-propane-2-sulfinic acid (2-amino-5-bromo-phenyl)-(4-chloro-phenyl)-methyleneamide

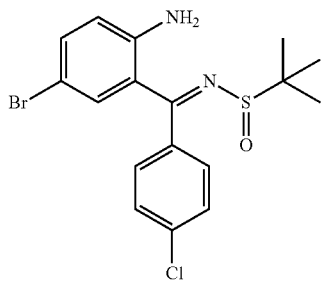 [SMILES: CC(C)(C)S(=O)/N=C(\c1ccc(Cl)cc1)c1cc(Br)ccc1N]

To a solution of (2-Amino-5-bromo-phenyl)-(4-chloro-phenyl)-methanone (13.87 g, 0.05 mol) in THF (200 mL) is added 2-Methyl-propane-2-sulfinic acid amide (6.5 g, 0.05 mol) and Ti(OEt)$_4$ (20.5 g, 0.09 mol). The stirred mixture is refluxed at 80° C. The mixture is quenched with H$_2$O, filtered. THF is removed, extracted with ethyl acetate, dried over NaSO$_4$ and concentrated then purified by silica gel. This produces the desired compound.
Yield: 11.0 g (59.5%)
HPLC-MS: M+H=413/415; t$_{Ret}$=2.36 min; AM12

2-Methyl-propane-2-sulfinic acid [(2-amino-5-bromo-phenyl)-(4-chloro-phenyl)-methyl]-amide

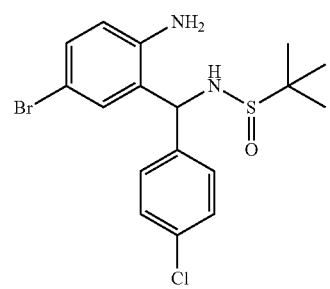 [SMILES: CC(C)(C)S(=O)NC(c1ccc(Cl)cc1)c1cc(Br)ccc1N]

To a solution of 2-Methyl-propane-2-sulfinic acid (2-amino-5-bromo-phenyl)-(4-chloro-phenyl)-methyleneamide (6.82 g, 0.02 mmol) dissolved in THF (196 mL) and H$_2$O (4 mL) is added NaBH$_4$ (1.57 g, 0.04 mol) at 0° C. The mixture is stirred at RT. The mixture is quenched with MeOH and H$_2$O, MeOH and THF is removed. The mixture is extracted with ethyl acetate, dried over NaSO$_4$ and concentrated. This provides the desired compound which is used without further purification.
Yield: 6.76 g (98.6%)

2-Methyl-propane-2-sulfinic acid [(2-amino-5-bromo-phenyl)-(4-chloro-phenyl)-methyl]-methyl-amide

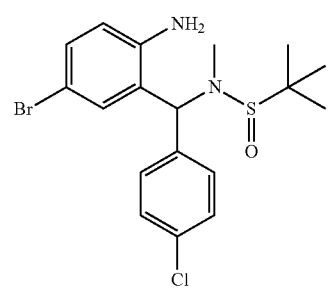 [SMILES: CN(C(c1ccc(Cl)cc1)c1cc(Br)ccc1N)S(=O)C(C)(C)C]

To a solution of 2-Methyl-propane-2-sulfinic acid [(2-amino-5-bromo-phenyl)-(4-chloro-phenyl)-methyl]-amide (9.73 g, 0.024 mmol) solved in 150 mL DMF is added LiHNDS (1.06M, 24.5 mL) at −30° C. After 1 h, methyl iodide (3.4 g, 0.024 mol) and triethylamine (33.5 mL, 0.24 mol) is added. The mixture is stirred at RT for 2 h. The mixture is then quenched with H$_2$O, extracted with CH$_3$O (CH$_3$)$_3$, dried over Na$_2$SO$_4$, concentrated. This produces the desired compound.
Yield: 9.00 g (89.5%)

4-Bromo-2-[(4-chloro-phenyl)-methylamino-methyl]-phenylamine

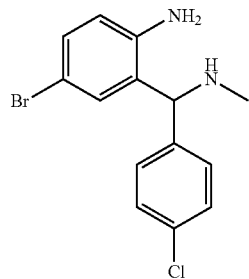 [SMILES: CNC(c1ccc(Cl)cc1)c1cc(Br)ccc1N]

To a solution of 2-Methyl-propane-2-sulfinic acid [(2-amino-5-bromo-phenyl)-(4-chloro-phenyl)-methyl]-methylamide (10 g, 0.023 mol) dissolved in 200 mL HCl/ethyl acetate is stirred at RT. The ethyl acetate is removed. The mixture is adjusted to pH10 by addition of NaOH aq. The mixture is extracted with ethyl acetate, dried over NaSO₄ and concentrated. The product is used in the next step without further purification.

Yield: 8.20 g

6-Bromo-4-(4-chloro-phenyl)-3-methyl-3,4-dihydro-1H-quinazolin-2-one

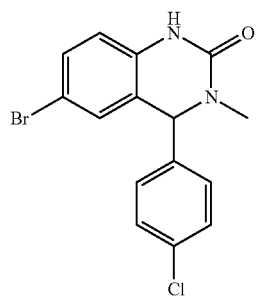 [SMILES: CN1C(=O)Nc2ccc(Br)cc2C1c1ccc(Cl)cc1]

To a solution of 4-Bromo-2-[(4-chloro-phenyl)-methylamino-methyl]-phenylamine (4.0 g, 0.012 mol) dissolved in THF (100 mL) is added triphosgene (4.4 g, 0.015 mol). The mixture is stirred at RT for 1 hours. The reaction is quenched with H₂O, extracted with ethyl acetate, dried over NaSO₄ and concentrated. This produces the desired compound.

Yield: 3.10 g (71.8%)
HPLC-MS: M+H=351/353; t$_{Ret}$=3.03 min; AM5

4-(4-Chloro-phenyl)-6-(3,5-dimethyl-isoxazol-4-yl)-3-methyl-3,4-dihydro-1H-quinazolin-2-one

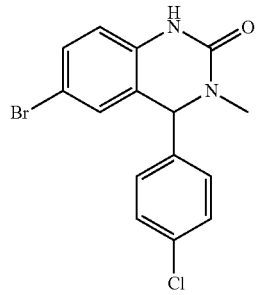 [SMILES: CN1C(=O)Nc2ccc(Br)cc2C1c1ccc(Cl)cc1]

To a solution of 6-Bromo-4-(4-chloro-phenyl)-3-methyl-3,4-dihydro-1H-quinazolin-2-one (0.2 g, 0.57 mmol) dissolved in dioxane (50 mL) is added 3,5-dimethylisoxazole-4-boronic acid (0.1 g, 0.74 mmol), PdCl₂ (0.048 g, 0.057 mmol) and Na₂CO₃ aq. The mixture is stirred at 120° C. to reflux for 5 hours. Then cooled to RT, concentrated and purified by column chromatography on silica gel to give the desired compound.

Yield: 70 mg (33.3%)
HPLC-MS: M+H=368; t$_{Ret}$=2.83 min; AM5

EXAMPLE 8

Preparation of 6-(3,5-Dimethyl-isoxazol-4-yl)-3-methyl-4-phenyl-3,4-dihydro-benzo[e][1,3]oxazin-2-one

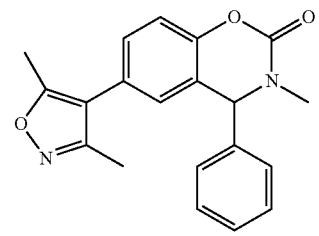 [SMILES: Cc1noc(C)c1-c1ccc2c(c1)C(c1ccccc1)N(C)C(=O)O2]

Reaction scheme

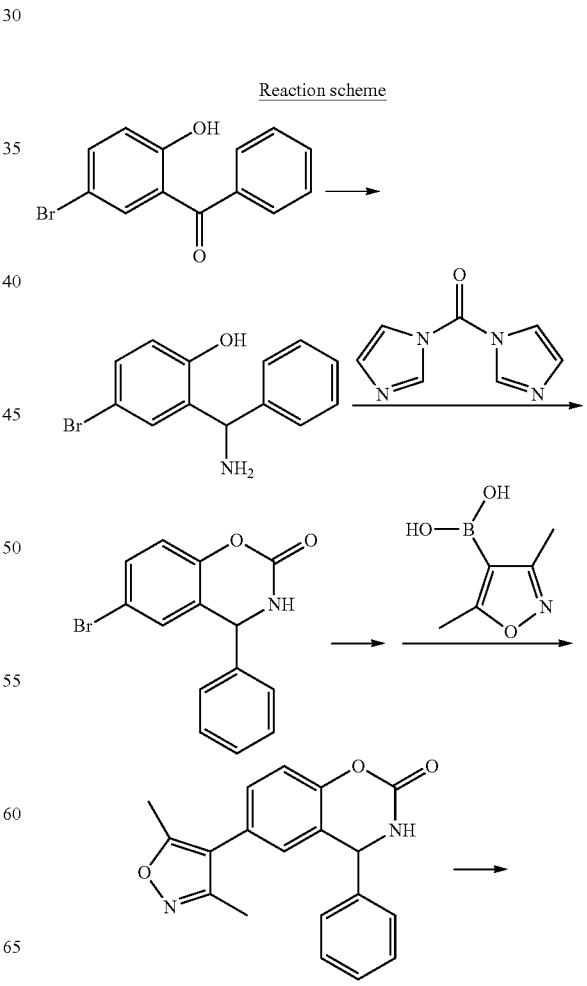

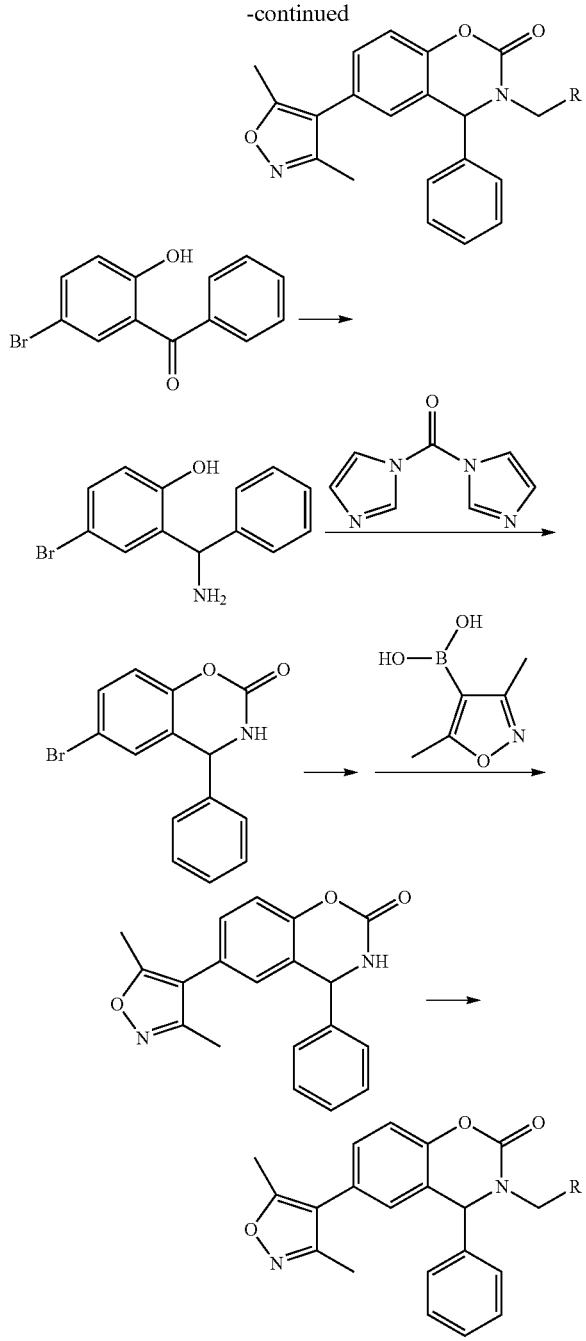

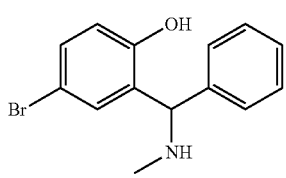 [SMILES: CNC(c1ccccc1)c1cc(Br)ccc1O]

4-Bromo-2-(methylamino-phenyl-methyl)-phenol (5-Bromo-2-hydroxy-phenyl)-phenyl-methanone (1.00 g, 3.536 mmol), 4 Å molecular sieves (1 g), and DCM are mixed then methylamine in THF (8.84 mL, 2M, 17.682 mmol) is added to followed by p-toluenesulfonic acid in acetic acid (0.474 mL, 12%, 0.354 mmol). Sodium triacetoxyborohydride (4.20 g, 19.80 mmol) is added in three separate portions. The mixture is quenched with saturated $Na_2CO_3$ solution and extracted with EtOAc. The organic phase is dried over $Na_2SO_4$ and the solvent removed on a rotary evaporator. This provides the desired compound which is used in the next step without further purification.

Yield: 1.10 g (107%)

HPLC-MS: M+H=292; $t_{Ret}$=1.32 min; AM1

6-Bromo-3-methyl-4-phenyl-3,4-dihydro-benzo[e][1,3]oxazin-2-one

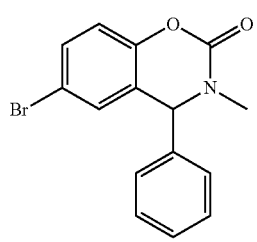 [SMILES: CN1C(=O)Oc2ccc(Br)cc2C1c1ccccc1]

4-Bromo-2-(methylamino-phenyl-methyl)-phenol (100 mg, 0.342 mmol) is dissolved in DCM (2 mL) at room temperature and N,N'-carbonyldiimidazole (166.5 mg, 1.027 mmol) and 4-dimethylaminopyridine (4.18 mg, 0.034 mmol) are added. The mixture is stirred for 1 hour. The solvent is removed on a rotary evaporator. The residue is purified by column chromatography on silica gel using a methanol, dichloromethane gradient. The product fractions are combined and the solvent removed to afford the desired product.

Yield: 93 mg (85.4%)

HPLC-MS: M+H=318; $t_{Ret}$=1.24 min; AM1

6-(3,5-Dimethyl-isoxazol-4-yl)-3-methyl-4-phenyl-3,4-dihydro-benzo[e][1,3]oxazin-2-one

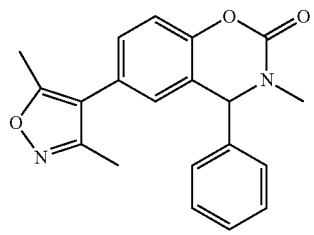 [SMILES: Cc1noc(C)c1-c1ccc2c(c1)C(c1ccccc1)N(C)C(=O)O2]

6-Bromo-3-methyl-4-phenyl-3,4-dihydro-benzo[e][1,3]oxazin-2-one (93 mg, 0.292 mmol) 3,5-dimethylisoxazole-4-boronic acid (53.55 mg, 0.380 mmol), $K_2CO_3$ (80.79 mg, 0.585 mmol) and tetrakis(triphenylphosphine)palladium(0) (67.55 mg, 0.058 mmol) dimethoxyethane (1.5 mL) and water (0.5 mL) are added to a microwave vial. This is purged with argon gas and stirred at 120° C. for 30 minutes. The reaction mixture is diluted with dichloromethane (20 mL) and saturated $NaHCO_3$ solution (3×5 mL). The organic phase is dried over $MgSO_4$, evaporated, and complete. The residue purified using SCX chromatography, the filtrate is concentrated. The residue is dissolved in ACN and purified by preparative HPLC. This affords the desired product.

Yield: 57 mg (58.3%)

HPLC-MS: M+H=335; $t_{Ret}$=1.17 min; AM1

EXAMPLE 9

Preparation of (S) 6-(3,5-Dimethyl-isoxazol-4-yl)-3-methyl-4-phenyl-3,4-dihydro-benzo[e][1,3]oxazin-2-one

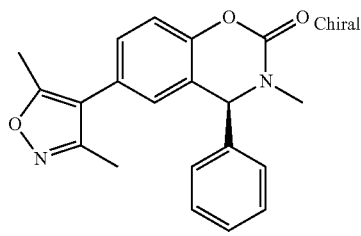 [SMILES: Cc1noc(C)c1-c1ccc2c(c1)[C@H](c1ccccc1)N(C)C(=O)O2]

Column: Daicel ChiralPak AD, 4.6×250 mm
Eluent: MeOH+0.1% DEA
Flow: 1 ml/min
Temperature: 40° C.

EXAMPLE 10

Preparation of 6-(3,5-Dimethyl-isoxazol-4-yl)-4-phenyl-1,4-dihydro-benzo[d][1,3]oxazin-2-one

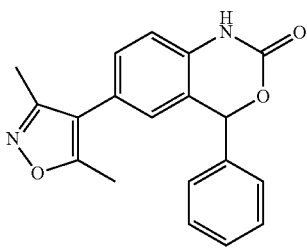 [SMILES: Cc1noc(C)c1-c1ccc2c(c1)C(c1ccccc1)OC(=O)N2]

(2-Amino-5-bromo-phenyl)-phenyl-methanol

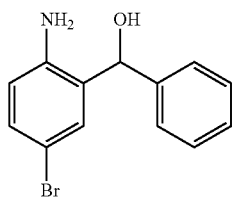 [SMILES: Nc1ccc(Br)cc1C(O)c1ccccc1]

(2-Amino-5-bromo-phenyl)-phenyl-methanone (4.00 g, 14.49 mmol) is dissolved in methanol (50 mL). Sodium borohydride (0.55 g, 14.49 mmol) is added in small portions over 45 minutes. The reaction mixture is stirred at room temperature overnight. Water (10 mL) is added and the mixture stirred at room temperature for 15 minutes. The solvent is removed and the residue purified by column chromatography on silica gel using a petrol ether/ethylacetate gradient. This affords the desired compound as a white solid.

Yield: 3.50 g (87%)

6-Bromo-4-phenyl-1,4-dihydro-benzo[d][1,3]oxazin-2-one

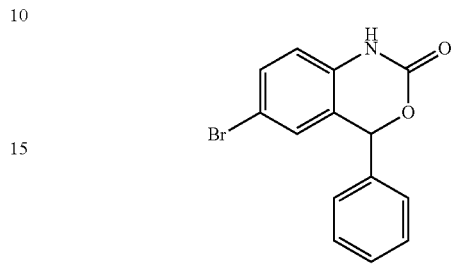

(2-Amino-5-bromo-phenyl)-phenyl-methanol (0.50 g, 1.798 mmol) is dissolved in anhydrous THF (25 mL). Triethylamine (0.55 g, 5.393 mmol) is added followed by triphosgene (0.16 g, 0.539 mmol). The mixture is stirred at room temperature overnight. Water (50 mL) is added and the reaction stirred for 15 minutes then extracted with ethylacetate (3×50 mL). The organic phases is washed with 1N HCl (2×50 mL) and a saturated solution of sodium hydrogencarbonate (50 mL). The organic phase is dried over sodium sulfate and concentrated in vacuo to provide the desired product as a white solid.

Yield: 0.46 g (84%).

6-(3,5-Dimethyl-isoxazol-4-yl)-4-phenyl-1,4-dihydro-benzo[d][1,3]oxazin-2-one

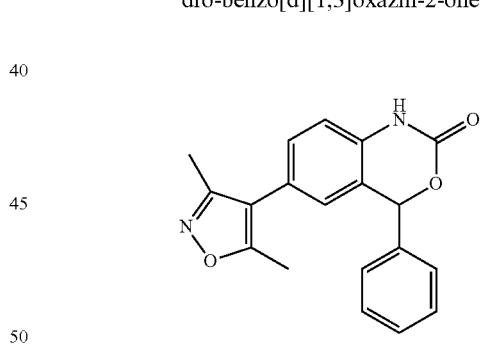

6-Bromo-4-phenyl-1,4-dihydro-benzo[d][1,3]oxazin-2-one (150 mg, 0.493 mmol), 3,5-dimethyl-4-isoxazolylboronic acid (208.5 mg, 1.480 mmol), 1,1'-bis(diphenylphosphino)ferocene-palladium(II)dichloride dichloromethane complex (80.5 mg, 0.099 mmol) are added to a microwave vessel. A saturated acqueous solution of sodium carbonate (1 mL) and dimethoxyethane (2 mL) are added. The vessel is purged with argon for 10 min. The reaction mixture is heated in a microwave reactor for 90 minutes. The mixture is filtered and the filter cake is washed with dichloromethane. The volatiles are removed on in vacuo and the residue purified by reversed phase HPLC.

Yield: 75 mg (47.5%)

HPLC-MS: M+H=321; $t_{Ret}$=1.09 min; AM1

EXAMPLE 11

Preparation of 6-(3,5-Dimethyl-isoxazol-4-yl)-4-phenyl-3-(tetrahydro-pyran-4-ylmethyl)-3,4-dihydro-benzo[e][1,3]oxazin-2-one

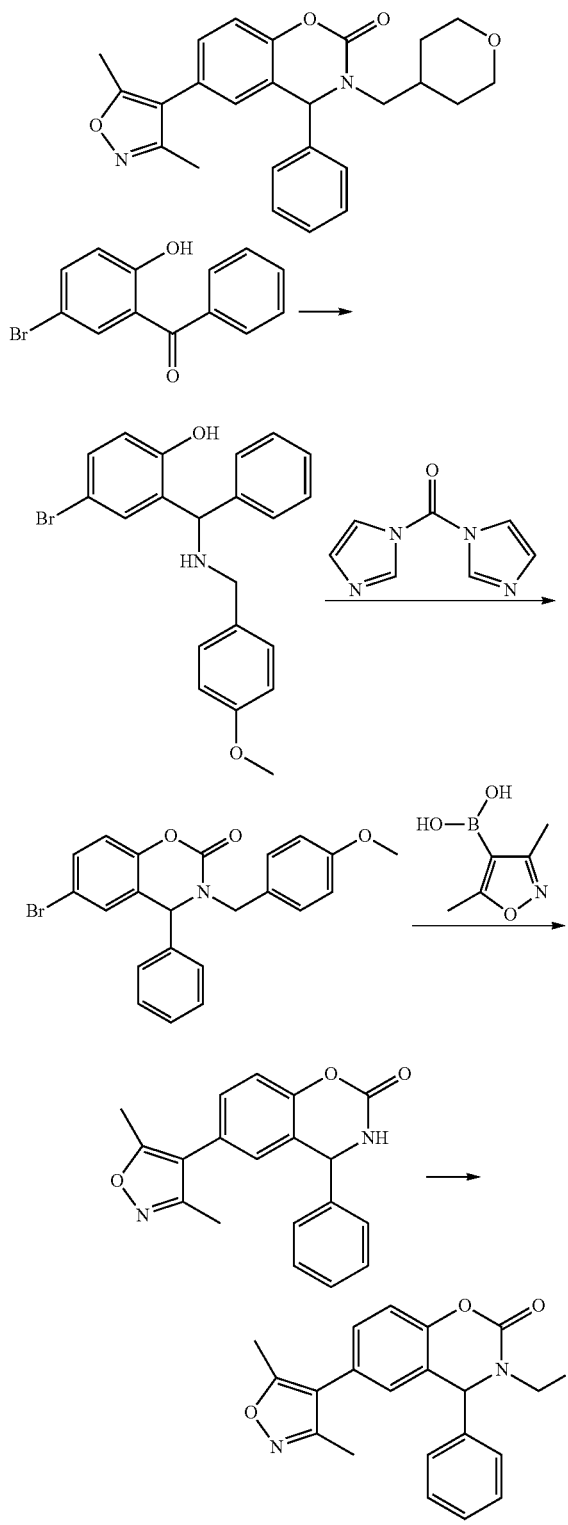

4-Bromo-2-[(4-methoxy-benzylamino)-phenyl-methyl]-phenol

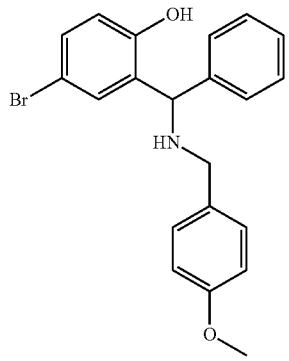 [SMILES: COc1ccc(CNC(c2ccccc2)c2cc(Br)ccc2O)cc1]

(5-Bromo-2-hydroxy-phenyl)-phenyl-methanone (5.0 g, 17.68 mmol) is dissolved in dichloromethane (20 mL). 4-Methoxybenzylamine (3.00 mL, 22.02 mmol) is added and the mixture stirred at room temperature for 2 hours. 4-Bromo-2-[(4-methoxy-benzylimino)-phenyl-methyl]-phenol (700 mg, 1.766 mmol) is dissolved in dichloromethane (6 mL) and treated with sodium triacetoxyborohydride (2.0 g, 8.96 mmol). The mixture is stirred at room temperature over the weekend. The mixture is poured into saturated aqueous sodium bicarbonate solution. The aqueous phase is exhaustively extracted with dichloromethane. The combined organic phases are dried over magnesium sulfate, the drying agent is filtered off. The filtrate is concentrated to dryness in vacuo. The residue is purified by column chromatography on silica gel using dichloromethane as an eluant. The product fractions are evaporated to dryness in vacuo. This affordes the desired compound as a colourless oil.

Yield: 560 mg (75.6%)

HPLC-MS: 277/279 $t_{Ret}$=0.82 min; AM1

6-Bromo-3-(4-methoxy-benzyl)-4-phenyl-3,4-dihydro-benzo[e][1,3]oxazin-2-one

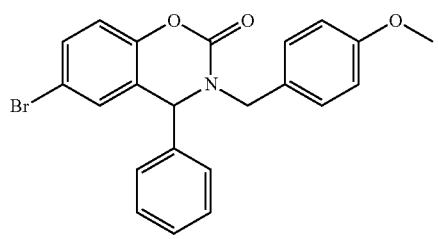 [SMILES: COc1ccc(CN2C(=O)Oc3ccc(Br)cc3C2c2ccccc2)cc1]

4-Bromo-2-[(4-methoxy-benzylamino)-phenyl-methyl]-phenol (500 mg, 1.255 mmol) is dissolved in dichloromethane (20 mL). N,N'-carbonyldiimidazole (250 mg, 1.496 mmol) is added and the mixture stirred at room temperature for 1 hour. The mixture is evaporated to dryness in vacuo and the residue is purified by column chromatography on silica gel using an ethylacetate cyclohexane gradient. The product fractions are evaporated to dryness in vacuo to give the desired product.

Yield: 465 mg (85.6%)

HPLC-MS: 424/426 $t_{Ret}$=1.15 min; AM1

6-Bromo-4-phenyl-3,4-dihydro-benzo[e][1,3]oxazin-2-one

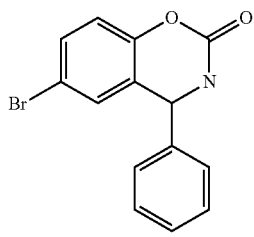 [SMILES: O=C1NC(c2ccccc2)c2cc(Br)ccc2O1]

4-Bromo-2-[(4-methoxy-benzylamino)-phenyl-methyl]-phenol (0.30 g, 0.693 mmol) is slurried in acetonitrile (3 mL). An aqueous solution of ceric ammonium nitrate (1.15 g, 2.10 mmol) is slowly added dropwise at room temperature. The reaction mixture is shaken at room temperature for 2 hours. The mixture is poured into an aqueous solution of sodium pyrosulfite and left for half an hour. The aqueous phase is exhaustively extracted with ethyl acetate. The combined organic phases were dried over magnesium sulfate. After evaporated to in vacuo the residue is triturated with acetonitrile. The insoluble product is collected by filtration and dried. This provides the desired product.

Yield: 116 mg (55%)
HPLC-MS: $t_{Ret}$=1.15 min; AM1

6-(3,5-Dimethyl-isoxazol-4-yl)-4-phenyl-3,4-dihydro-benzo[e][1,3]oxazin-2-one

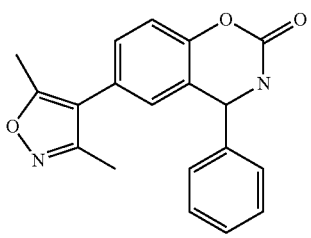

To a solution of 6-Bromo-4-phenyl-3,4-dihydro-benzo[e][1,3]oxazin-2-one (90 mg, 0.296 mmol) in 1,2-dimethoxyethane (3 mL) is added saturated $Na_2CO_3$ in water (3 mL), 3,5-dimethylisoxazole-4-boronic acid (90 mg, 0.607 mmol) and Pd(dppf)Cl$_2$ (13.5 mg, 0.016 mml) The mixture is refluxed at 100° C. overnight.

The reaction is concentrated and is purified by chromatography on silica gel to give the desired product.

Yield: 65 mg (69%)
HPLC-MS: M+H=343; $t_{Ret}$=1.07 min; AM1

6-(3,5-Dimethyl-isoxazol-4-yl)-4-phenyl-3-(tetrahydro-pyran-4-ylmethyl)-3,4-dihydro-benzo[e][1,3]oxazin-2-one

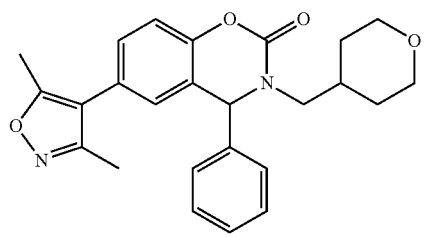 [SMILES: Cc1noc(C)c1-c1ccc2c(c1)C(c1ccccc1)N(CC1CCOCC1)C(=O)O2]

6-(3,5-Dimethyl-isoxazol-4-yl)-4-phenyl-3,4-dihydro-benzo[e][1,3]oxazin-2-one (20 mg, 0.06 mmol) is dissolved in DMF 0.5 mL. Sodium hydride (60% w/w, 2.6 mg, 0.065 mmol) is added. The mixture is cooled in an ice bath. 4-bromomethyltetrahydropyran (14 mg, 0.074 mmol) is added and the mixture stirred and allowed to warm to room temperature over night. Sodium hydride (0.5 mg, 0.013 mmol) is added and the mixture stirred at room temperature for a further 3 hours. The mixture is quenched by the addition of water (1 mL). The solvent is removed in vacuo and the residue is purified by preparative HPLC. The product fraction is lyophilized to produce the desired product as a yellow solid.

Yield: 1.2 mg (4.6%)
HPLC-MS: M+H=419; $t_{Ret}$=1.33 min; AM1

EXAMPLE 12

6-(3,5-Dimethyl-isoxazol-4-yl)-3-(4-methoxy-benzyl)-4-phenyl-3,4-dihydro-benzo[e][1,3]oxazin-2-one

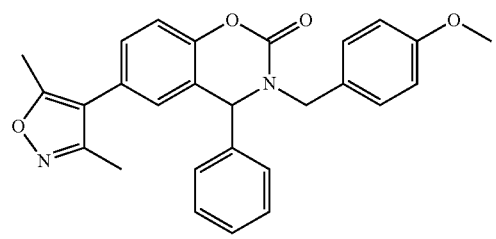 [SMILES: COc1ccc(CN2C(=O)Oc3ccc(-c4c(C)noc4C)cc3C2c2ccccc2)cc1]

Prepared from 6-Bromo-3-(4-methoxy-benzyl)-4-phenyl-3,4-dihydro-benzo[e][1,3]oxazin-2-one using analogous method to above.

Yield: 42 mg (67.4%)
HPLC-MS: M+H=441; $t_{Ret}$=1.59 min; AM1

EXAMPLE 13

Preparation of 6-(3,5-Dimethyl-isoxazol-4-yl)-3-methyl-4-pyridin-2-yl-3,4-dihydro-1H-quinazolin-2-one

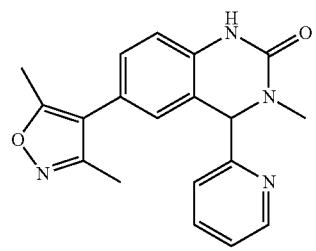

(2-Amino-5-bromo-phenyl)-pyridin-2-yl-methanone

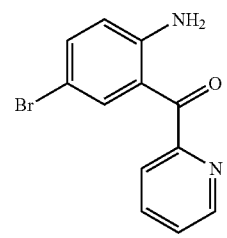 [SMILES: Nc1ccc(Br)cc1C(=O)c1ccccn1]

To a −40° C. solution of 2.5 M n-BuLi (18 mL) in THF (300 mL) is added 2-bromopyridine (5.0 g, 32 mmol) over 15 min. The reaction is stirred for 1 h at −40° C., and then treated with 2-Amino-5-bromo-benzoic acid (6.9 g, 32 mmol) in THF (300 mL). The reaction is warmed to 0° C. and stirred for 2 h then quenched with TMSCl (3.4 g, 32 mmol). The reaction is stirred at room temperature for 30 min then cooled to 0° C. and quenched with 3M HCl (20 mL). The aqueous layer is separated and the organic layer is extracted with 3M HCl. The organic layer is basified with solid NaOH, the resulting mixture is extracted with EtOAc, and the organic layer is dried over Na₂SO₄, filtered and concentrated. The residue is purified by column chromatography on silica gel to give the desired product as a yellow solid.

Yield: 5.50 g (62.7%)
HPLC-MS: M+H=277/279; $t_{Ret}$=3.16 min; AM6

4-Bromo-2-(methylamino-pyridin-2-yl-methyl)-phenylamine

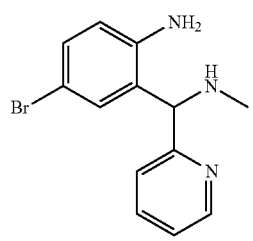 [SMILES: CNC(c1ccccn1)c1cc(Br)ccc1N]

To a solution of (2-Amino-5-bromo-phenyl)-pyridin-2-yl-methanone (500 mg, 1.8 mmol) in MeOH (20 mL) is added Ti(i-OPr)₄ (1.0 g, 3.6 mmol) and methylamine (2M in THF, 4.5 mL). Then the mixture is stirred at room temperature for 6 h. Sodium borohydride (137 mg, 3.6 mmol) is added in one portion. The mixture is stirred at room temperature for 2 h. Water (10 mL) is added and the mixture is filtered and washed with EtOAc. The filtrate is washed with brine, the organic layer is concentrated in vacuum to give the desired product as a crude mixture. This is used in next step with no further purification.

Yield: 500 mg
HPLC-MS: M+H=292/294; $t_{Ret}$=0.96 min; AM12

6-Bromo-3-methyl-4-pyridin-2-yl-3,4-dihydro-1H-quinazolin-2-one

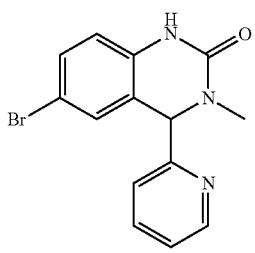

To a solution of crude 4-Bromo-2-(methylamino-pyridin-2-yl-methyl)-phenylamine (500 mg) in THF (20 mL) is added triphosgene (493 mg, 1.87 mmol), then the mixture is stirred at room temperature for 2 h. TLC showed the reaction is completed. Water (20 mL) is added and the mixture is extracted with EtOAc, the organic layer is dried over Na₂SO₄ and concentrated to give the desired compound as a crude mixture. This is used in next step with no further purification.

Yield: 600 mg
HPLC-MS: M+H=441; $t_{Ret}$=1.59 min; AM1

6-(3,5-Dimethyl-isoxazol-4-yl)-3-methyl-4-pyridin-2-yl-3,4-dihydro-1H-quinazolin-2-one

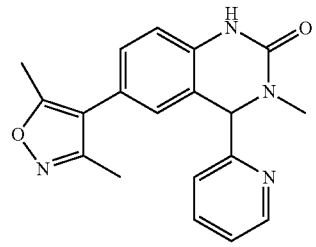

To a solution of crude 6-Bromo-3-methyl-4-pyridin-2-yl-3,4-dihydro-1H-quinazolin-2-one (600 mg, 0.002 mol) in DME/H₂O (12 mL/4 mL) is added 3,5-dimethylisoxazole-4-boronic acid (265 mg, 0.002 mol), Pd(PPh₃)₄ (77 mg, 0.08 mmol) and Na₂CO₃ (332 mg, 3.14 mmol). After addition, the mixture is refluxed for 3 h. The mixture is concentrated in vacuum and the residue is purified by preparative HPLC to give the desired product as a yellow solid.

Yield: 100 mg (19%, 3 steps)
HPLC-MS: M+H=335; $t_{Ret}$=2.30 min; AM1

EXAMPLE 14

Preparation of (R) 6-(3,5-Dimethyl-isoxazol-4-yl)-3-methyl-4-pyridin-2-yl-3,4-dihydro-benzo[e][1,3]oxazin-2-one

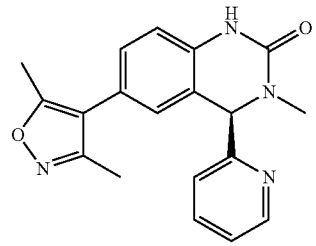

Column: Daicel ChiralPak AD, 4.6×250 mm
Eluent: MeOH+0.1% DEA
Flow: 1 ml/min
Temperature: 40° C.

EXAMPLE 15

Preparation of 6-(3,5-Dimethyl-isoxazol-4-yl)-3-methyl-4-phenyl-3,4-dihydro-1H-pyrido[3,4-d]pyrimidin-2-one

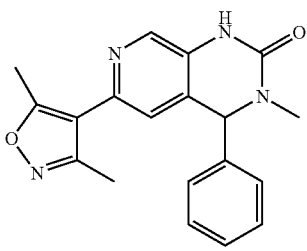

Reaction scheme:

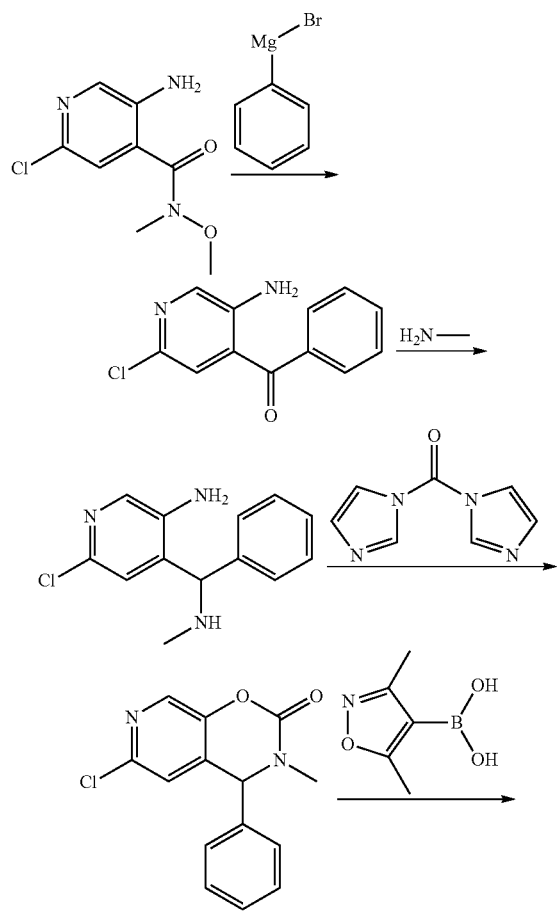

5-Amino-2-chloro-N-methoxy-N-methyl-isonicotinamide

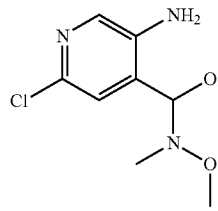

5-Amino-2-chloro-isonicotinic acid (109 mg, 0.600 mmol), N,O-dimethylhydroxylamine hydrochloride (62 mg, 0.617 mmol), 1,1'-carbonyldiimidazole (131 mg, 0.800 mmol) and diisopropylethamine (0.38 mL, 2.200 mmol) are stirred in DMSO (1 mL) at room temperature overnight. The mixture is diluted with water then the aqueous phase is extracted with dichloromethane. The organic phase is dried over magnesium sulfate and the solvent is concentrated to dryness. The residue is purified using silica gel chromatography (dichloromethane/methanol gradient). This provides the desired compound.
Yield: 103.5 mg (80%)
HPLC-MS: M+H=216/218; $t_{Ret}$=0.43 min; AM1

(5-Amino-2-chloro-pyridin-4-yl)-phenyl-methanone

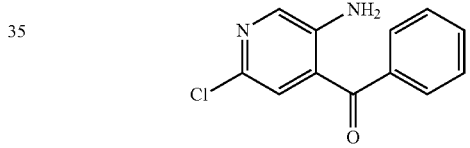

To 5-Amino-2-chloro-N-methoxy-N-methyl-isonicotinamide (1.50 g, 6.608 mmol) in THF (25 mL) under argon is added phenylmagnesium bromide in diethyl ether (6.00 mL, 2M, 18 mmol) at 0° C. The mixture is stirred for 30 minutes at 0° C. Aqueous citric acid solution (1 M, 25 mL) is added to the reaction and the mixture is extracted with ethyl acetate, the organic phase is dried over magnesium sulfate. The drying agent is removed by filtration and the solvent is concentrated to dryness. This provides the desired compound which is used without further purification.
Yield: 1.44 g (93.7%)
HPLC-MS: M+H=233/235; $t_{Ret}$=0.57 min; AM1

6-Chloro-4-(methylamino-phenyl-methyl)-pyridin-3-ylamine

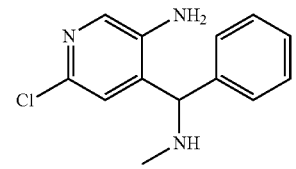 [SMILES: CNC(c1ccccc1)c1cc(Cl)ncc1N]

(5-Amino-2-chloro-pyridin-4-yl)-phenyl-methanone (360 mg, 1.547 mmol), methylamine in THF (4.5 mL, 2 M, 9.00 mmol), p-toluene sulfonic acid in acetic acid (225 mg, 12%, 0.157 mmol) are stirred at room temperature in dichloromethane (15 mL). Sodium triacetoxyborohydride (1.92 g, 9.06 mmol) is added in three separate portions over 24 hours. The reaction mixture is quenched with saturated sodium carbonate solution and extracted with ethyl acetate. The organic phase is dried over magnesium sulfate. The drying agent is removed by filtration. The solvent is removed in vacuo and the residue is purified by column chromatography on silica gel using a dichloromethane and methanol gradient. This provides the desired compound as a yellow solid.

Yield: 310 mg (64.7%)

HPLC-MS: M+H=248/250; $t_{Ret}$=0.15 min; AM10

6-Chloro-3-methyl-4-phenyl-3,4-dihydro-1H-pyrido[3,4-d]pyrimidin-2-one

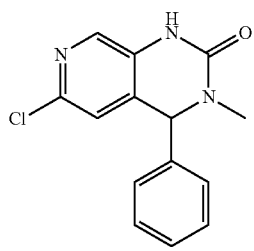 [SMILES: CN1C(=O)Nc2cnc(Cl)cc2C1c1ccccc1]

6-Chloro-4-(methylamino-phenyl-methyl)-pyridin-3-ylamine (100 mg, 0.323 mmol) and 1,1'-carbonyl-diimidazole (100 mg, 0.586 mmol) are stirred in THF (5 mL) at room temperature for 1.5 hours. The reaction mixture is added to water and the aqueous phase extracted with dichloromethane. The organic phase is dried over magnesium sulfate. The solvent is removed in vacuo and the residue purified by column chromatography on silica gel using a dichloromethane/methanol gradient. The product fractions are evaporated to dryness to provide the desired compound.

Yield: 64 mg (57.9%)

HPLC-MS: M+H=274/276; $t_{Ret}$=0.49 min; AM10

6-(3,5-Dimethyl-isoxazol-4-yl)-3-methyl-4-phenyl-3,4-dihydro-1H-pyrido[3,4-d]pyrimidin-2-one

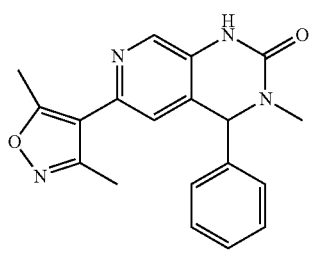 [SMILES: Cc1noc(C)c1-c1cc2c(cn1)NC(=O)N(C)C2c1ccccc1]

3,5-dimethylisoxazole-4-boronic acid (140 mg, 0.993 mmol), cesium carbonate (500 mg, 1.519 mmol) and 1,1-bis(diphenylphosphino)ferocene-palladium(II)dichloride dichloromethane complex are added to a microwave vessel flushed with argon. Dimethyl sulfoxide (5 mL) is added and the mixture purged with argon. Finally, 6-Chloro-3-methyl-4-phenyl-3,4-dihydro-1H-pyrido[3,4-d]pyrimidin-2-one (140 mg, 0.511 mmol) is added and the mixture again purged with argon and heated in a microwave oven at 90° C. for 120 minutes. The mixture is poured onto water and the aqueous phase extracted with dichloromethane. The organic phase is dried over magnesium sulfate. The drying agent is removed by filtration. The filtrate is concentrated to dryness and purified by chromatography on silica gel using a dichloromethane/methanol gradient. The product fractions are evaporated to dryness and purified by reverse phase HPLC. This affordes the desired product as a white solid.

Yield: 31 mg (18.1%)

HPLC-MS: M+H=335; $t_{Ret}$=0.98 min; AM1

EXAMPLE 16

Preparation of (S) 6-(3,5-Dimethyl-isoxazol-4-yl)-3-methyl-4-phenyl-3,4-dihydro-1H-pyrido[3,4-d]pyrimidin-2-one

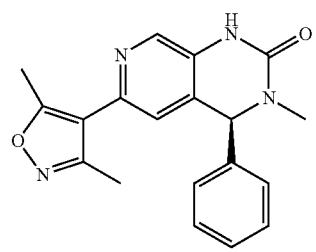 [SMILES: Cc1noc(C)c1-c1cc2c(cn1)NC(=O)N(C)[C@H]2c1ccccc1]

Column: Daicel ChiralPak AD, 4.6×250 mm
Eluent: MeOH+0.1% DEA
Flow: 1 ml/min
Temperature: 40° C.

EXAMPLE 17

Preparation of 6-(3,5-Dimethyl-isoxazol-4-yl)-3-methyl-4-phenyl-3,4-dihydro-1H-pyrido[3,2-d]pyrimidin-2-one

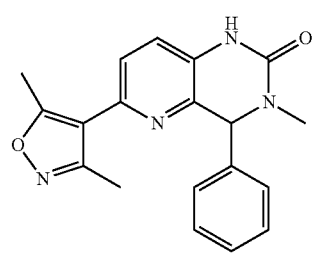 [SMILES: Cc1noc(C)c1-c1ccc2c(n1)C(c1ccccc1)N(C)C(=O)N2]

Analogous method used to preparation of 6-(3,5-Dimethyl-isoxazol-4-yl)-3-methyl-4-phenyl-3,4-dihydro-1H-pyrido[3,4-d]pyrimidin-2-one.

Yield: 15 mg (36%)

HPLC-MS: M+H=335; $t_{Ret}$=1.03 min; AM1

EXAMPLE 18

Preparation of 6-(3,5-Dimethyl-isoxazol-4-yl)-3-methyl-4-phenyl-3,4-dihydro-1H-pyrido[2,3-]pyrimidin-2-one

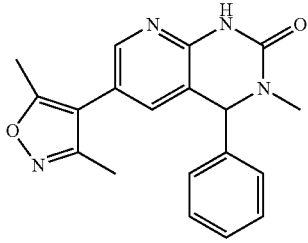 [SMILES: Cc1noc(C)c1-c1cnc2c(c1)C(c1ccccc1)N(C)C(=O)N2]

Analogous method used to preparation of 6-(3,5-Dimethyl-isoxazol-4-yl)-3-methyl-4-phenyl-3,4-dihydro-1H-pyrido[3,4-d]pyrimidin-2-one.
Yield: 11 mg (7.5%)
HPLC-MS: M+H=335; $t_{Ret}$=1.00 min; AM1

EXAMPLE 19

Preparation of 6-(3,5-Dimethyl-isoxazol-4-yl)-3,4-dimethyl-4-phenyl-3,4-dihydro-1H-quinazolin-2-one

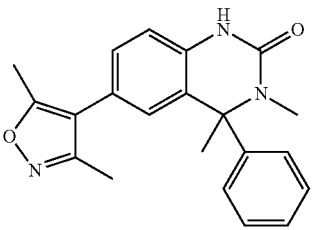 [SMILES: Cc1noc(C)c1-c1ccc2c(c1)C(C)(c1ccccc1)N(C)C(=O)N2]

Reaction scheme

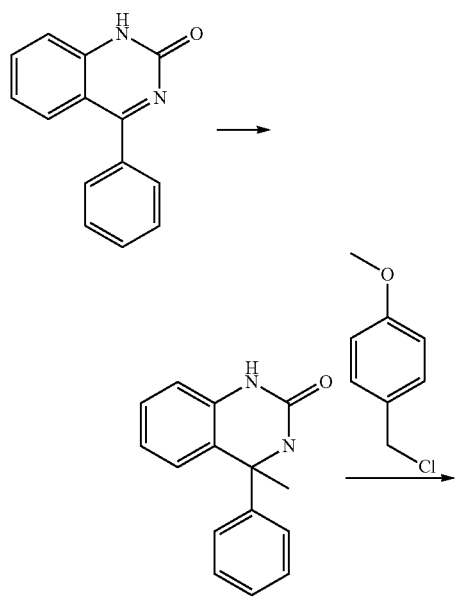

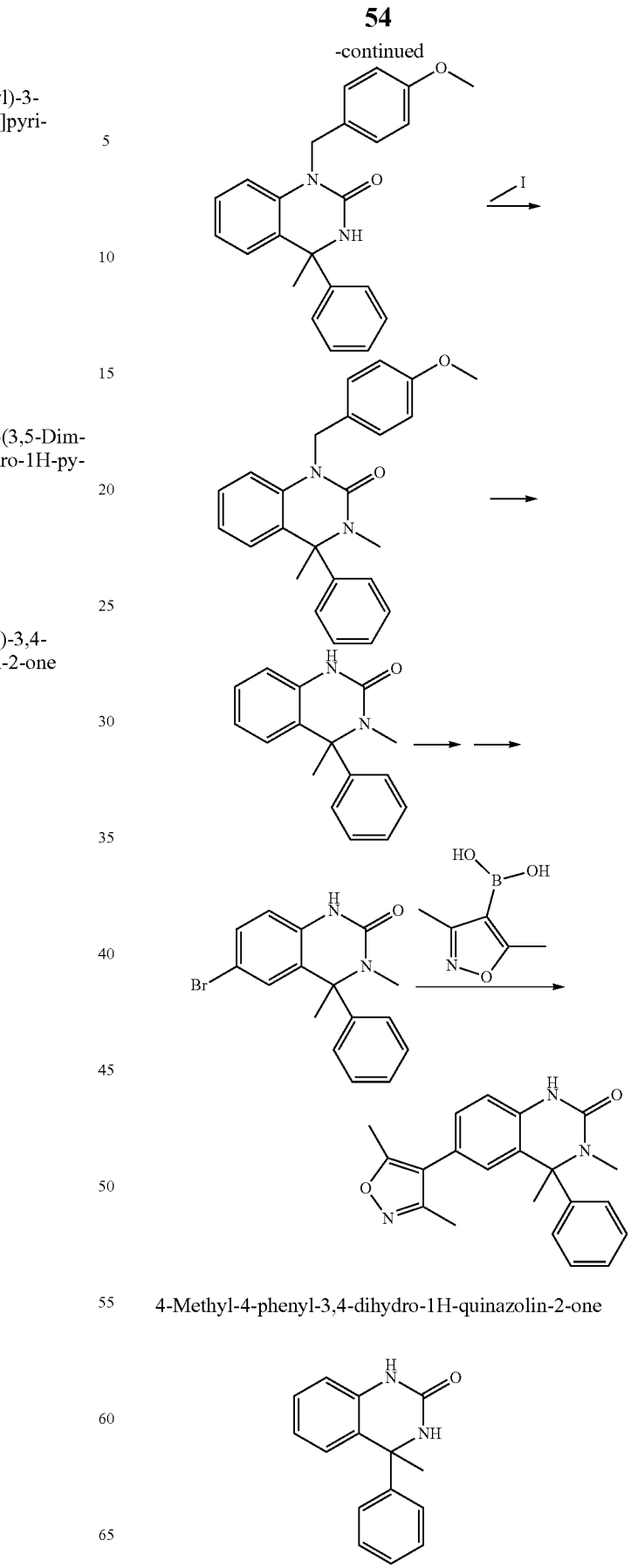

4-Methyl-4-phenyl-3,4-dihydro-1H-quinazolin-2-one

To a solution of 4-Phenyl-1H-quinazolin-2-one (5.0 g, 4.5 mmol) in THF (50 ml) is added methylmagnesium bromide (15.0 ml) dropwise at −78° C. under nitrogen. The mixture is stirred overnight at room temperature. The mixture is poured into an aqueous solution of $NH_4Cl$ and then extracted with EtOAc. The organic phase is washed with brine, dried over $Na_2SO_4$, filtered and evaporated under reduced pressure. The residue is purified on silica gel to give product as a white solid.

Yield: 4.0 g (75%)
TLC (1:1, petrol ether/ethyl acetate) Rf=0.4
HPLC-MS: M+H=239; $t_{Ret}$=2.24 min; AM2

1-(4-Methoxy-benzyl)-4-methyl-4-phenyl-3,4-dihydro-1H-quinazolin-2-one

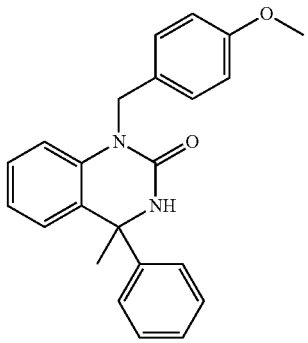 [SMILES: COc1ccc(CN2C(=O)NC(C)(c3ccccc3)c3ccccc32)cc1]

To a solution of 4-Methyl-4-phenyl-3,4-dihydro-1H-quinazolin-2-one (0.70 g, 2.9 mmol) in DMF (10 mL) is added 1-chloromethyl-4-methoxy-benzene and $Cs_2CO_3$ (1.92 g, 5.9 mmol). After the addition the mixture is stirred at −20° C. for 1 h. Then $CH_3I$ (2.6 g, 18 mmol) is added dropwise. After the addition the mixture is heated to refluxed overnight. $H_2O$ is then added and the mixture extracted with EtOAc which is dried over $Na_2SO_4$ and concentrated. The residue is purified by chromatography on silica gel to give product.

Yield 1.0 g (95%)
TLC (3:1, petrol ether/ethyl acetate) Rf=0.4
HPLC-MS: M+H=359; $t_{Ret}$=3.30 min; AM2

1-Benzyl-3,4-dimethyl-4-phenyl-3,4-dihydro-1H-quinazolin-2-one

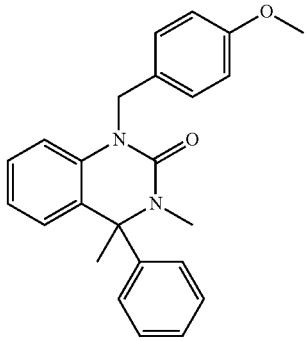 [SMILES: COc1ccc(CN2C(=O)N(C)C(C)(c3ccccc3)c3ccccc32)cc1]

A mixture of 1-Benzyl-4-methyl-4-phenyl-3,4-dihydro-1H-quinazolin-2-one (1.0 g, 2.8 mmol) in DMF (800 mL) is cooled to 0° C., then NaH (0.134 g, 3.35 mmol) is added. After the addition the mixture is stirred at 0° C. for 0.5 h. Then $CH_3I$ (0.79 g, 5.6 mmol) is added and the mixture is stirred at r.t. overnight. Then the mixture is poured into $NH_4Cl$ (30 mL) and is extracted with EtOAc, dried over $Na_2SO_4$ and concentrated to give product. This is used in the next step without further purification.

Yield: 1.0 g (96%)
TLC (3:1, petrol ether/ethyl acetate) Rf=0.6
HPLC-MS: M+H=373; $t_{Ret}$=3.76 min; AM2

3,4-Dimethyl-4-phenyl-3,4-dihydro-1H-quinazolin-2-one

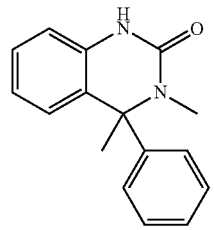 [SMILES: CN1C(=O)Nc2ccccc2C1(C)c1ccccc1]

To a solution of 1-(4-Methoxy-benzyl)-3,4-dimethyl-4-phenyl-3,4-dihydro-1H-quinazolin-2-one (1.00 g, 2.6 mmol) in trifluoroacetic acid (8 mL) and DCM (8 mL) is stirred at room temperature for 1 h. Then $H_2O$ is added and is extracted with $DCM/H_2O$. The organic layer is concentrated and is purified by chromatography on silica gel to give product.

Yield: 0.4 g (59%)
TLC (3:1, petrol ether/ethyl acetate) Rf=0.5
HPLC-MS: M+H=253; $t_{Ret}$=2.67 min; AM2

6-Bromo-3,4-dimethyl-4-phenyl-3,4-dihydro-1H-quinazolin-2-one

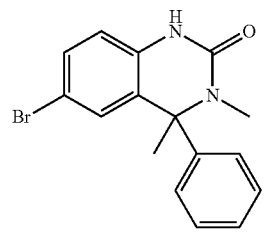 [SMILES: CN1C(=O)Nc2ccc(Br)cc2C1(C)c1ccccc1]

To a solution of 3,4-Dimethyl-4-phenyl-3,4-dihydro-1H-quinazolin-2-one (0.4 g, 1.59 mmol) in DCM (5 mL) is added NBS (0.28 g, 1.59 mmol). After the addition the mixture is stirred at room temperature overnight. The mixture is diluted with DCM, washed with $H_2O$, dried over anhydrous $Na_2SO_4$, filtered and concentrated. The residue is purified by chromatography on silica gel to give product.

Yield: 0.2 g (38%)
TLC (3:1, petrol ether/ethyl acetate) Rf=0.3
HPLC-MS: M+H=331/333; $t_{Ret}$=2.94 min; AM2

6-(3,5-Dimethyl-isoxazol-4-yl)-3,4-dimethyl-4-phenyl-3,4-dihydro-1H-quinazolin-2-one

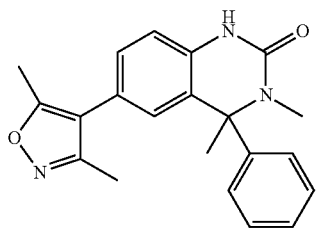 [SMILES: Cc1noc(C)c1-c1ccc2c(c1)C(C)(c1ccccc1)N(C)C(=O)N2]

To a solution of 6-Bromo-3,4-dimethyl-4-phenyl-3,4-dihydro-1H-quinazolin-2-one (140 mg, 0.42 mmol) in dioxane (10 mL) is added $Na_2CO_3$ (67 mg, 0.64 mmol) and 3,5-dimethylisoxazole-4-boronic acid (78 mg, 0.55 mmol) and $Pd(dppf)Cl_2$ then the mixture is refluxed at 100° C. overnight. The reaction is concentrated and is purified by chromatography on silica gel to give the desired product.

Yield: 51.6 mg (34%)

HPLC-MS: M+H=348; $t_{Ret}$=2.75 min; AM5

EXAMPLE 20

Preparation of 6-(3-Methoxy-5-methyl-isoxazol-4-yl)-3-methyl-4-phenyl-3,4-dihydro-1H-quinazolin-2-one

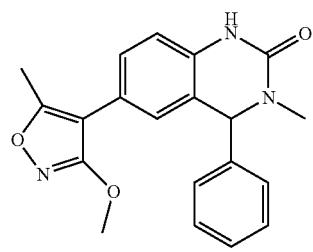 [SMILES: COc1noc(C)c1-c1ccc2c(c1)C(c1ccccc1)N(C)C(=O)N2]

3-Methoxy-5-methyl-isoxazole

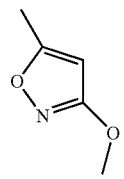

To a solution of compound 5-Methyl-isoxazol-3-one (0.5 g, 5.0 mmol) and $Ag_2O$ (1.1 g, 10.0 mmol) in DMF (15 mL) is added iodomethane (0.7 g, 5.0 mmol) at room temperature. Then the reaction mixture is stirred at room temperature for 2 h. The mixture is concentrated in vacuo to give product as an oil without further purification.

Yield: 0.60 g crude

4-Iodo-3-methoxy-5-methyl-isoxazole

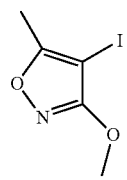

To a solution of 3-Methoxy-5-methyl-isoxazole (0.60 g, 5.0 mmol) in AcOH (15 mL) is added N-iodosuccinimide (1.10 g, 5.00 mmol) at 60° C. under nitrogen. Then the reaction mixture is stirred at 60° C. for 2 h. The mixture is concentrated in vacuo to give an oil. This oil is purified by column chromatography on silica gel to give the desired compound.

Yield: 240 mg (20%)

3-Methyl-4-phenyl-6-(4,4,5,5-tetramethyl-[1,3,2]dioxaborolan-2-yl)-3,4-dihydro-1H-quinazolin-2-one

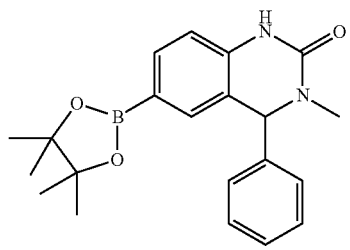

6-Bromo-3-methyl-4-phenyl-3,4-dihydro-1H-quinazolin-2-one (1000 mg, 3.13 mmol), bis(pinacolato)diboron (899 mg, 3.00 mmol), potassium acetate (938 mg, 9.00 mmol) and 1,1-bis(diphenylphosphino)ferrocene-palladium(II)dichloride dichloromethane complex (115 mg, 0.157 mmol) are added to a microwave vial. Dioxane (5 mL) is added and the vessel flushed with argon and then reacted overnight at 70° C. The mixture is extracted with DCM from water, and the residue is then purified using column chromatography on silica gel using a dichloromethane methanol gradient.

Yield: 1530 mg (crude).

HPLC-MS: M+H=356; $t_{Ret}$=1.29 min; AM1

6-(3-Methoxy-5-methyl-isoxazol-4-yl)-3-methyl-4-phenyl-3,4-dihydro-1H-quinazolin-2-one

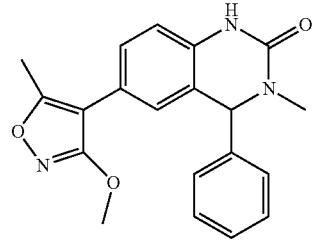

3-Methyl-4-phenyl-6-(4,4,5,5-tetramethyl-[1,3,2]dioxaborolan-2-yl)-3,4-dihydro-1H-quinazolin-2-one (457 mg, 1.255 mmol), 4-Iodo-3-methoxy-5-methyl-isoxazole (150 mg, 0.628 mmol), potassium carbonate (173 mg, 1.255 mmol) and Pd(dppf)Cl$_2$ (102.5 mg, 0.126 mmol) are added to a microwave vessel. Dimethoxyethane (0.1 mL) and water (0.1 mL) are added and the vessel flushed with argon. The mixture is heated in a microwave reactor at 120° C. for 3.5 hours. The reaction mixture is extracted with ethyl acetate from water. The organic phase is dried over Na2SO4 and the solvent is removed on a rotary evaporator. The residue is purified by reversed phase HPLC.

Yield: 20 mg (9%)

HPLC-MS: M+H=350; $t_{Ret}$=1.10 min; AM1

EXAMPLE 21

Preparation of 6-(3,5-Dimethyl-isoxazol-4-yl)-5-methoxy-3-methyl-4-phenyl-3,4-dihydro-1H-quinazolin-2-one

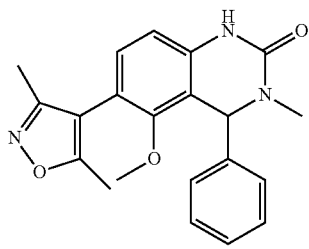 [SMILES: COc1c(-c2c(C)noc2C)ccc2c1C(c1ccccc1)N(C)C(=O)N2]

(2-Amino-6-methoxy-phenyl)-methanol

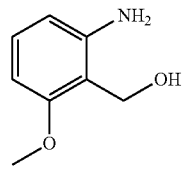

A mixture of LiAlH$_4$ (6.826 g, 0.018 mol) and THF (300 mL) is stirred at 0° C. 2-amino-6-methoxy-benzoic acid (15 g, 0.09 mol) in THF (150 mL) is added to the reaction mixture. The mixture is stirred at room temperature for 3 h. The reaction is quenched by the addition of water. 250 mL of 10% NaOH solution is then added and extracted from water with ethylacetate to give the desired product.

Yield: 12.6 g, (92%)

2-Amino-6-methoxy-benzaldehyde

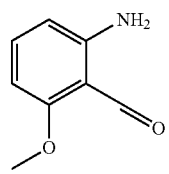

A mixture of (2-Amino-6-methoxy-phenyl)-methanol (5.00 g, 0.033 mol) and manganese dioxide (13.7 g) in DCM (500 mL) iswas stirred at 25° C. for 24 h. The resulting solid is filtered off, washed with DCM to give the desired product.

Yield: 4.0 g, (82%)

2,2,2-Trichloro-N-(2-formyl-3-methoxy-phenyl)-acetamide

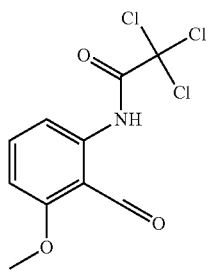 [SMILES: COc1cccc(NC(=O)C(Cl)(Cl)Cl)c1C=O]

A mixture of 2-Amino-6-methoxy-benzaldehyde (6.00 g, 0.04 mol) and triethylamine (4.4 g, 0.044 mol) is dissolved in THF (20 mL) and cooled to 0° C., then CCl$_3$COCl (7.95 g, 0.044 mol) is added and stirred at 25° C. for 24 h. The mixture is extracted from water with ethylacetate to give the desired product.

Yield: 5.0 g, (60%)

5-Methoxy-1H-quinazolin-2-one

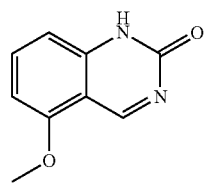

A mixture of 2,2,2-Trichloro-N-(2-formyl-3-methoxy-phenyl)-acetamide (6.6 g, 0.022 mol) and NH$_4$OAc (17.2 g, 0.22 mol) in t-BuOH (100 mL) is stirred and refluxed under nitrogen for 24 h. At the end of the reaction, the mixture is evaporated and extracted into DCM from water to give product.

Yield: 3.5 g, (92%)

5-Methoxy-4-phenyl-3,4-dihydro-1H-quinazolin-2-one

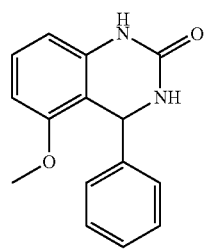 [SMILES: COc1cccc2c1C(c1ccccc1)NC(=O)N2]

Phenyl magnesium bromide (35.17 g, 0.19 mol) is added into a solution of reagent 1 (5.7 g, 0.032 mol) and THF (200 mL) at −60° C. in portions during a period of 50 min. The reaction mixture is stirred at 25° C. for 18 h. The solution is added in aqueous solution of NH$_4$Cl. The residue is partitioned by EA and wash MeOH to give product Yield: 3.20 g, (40%)

5-Methoxy-1-(4-methoxy-benzyl)-4-phenyl-3,4-dihydro-1H-quinazolin-2-one

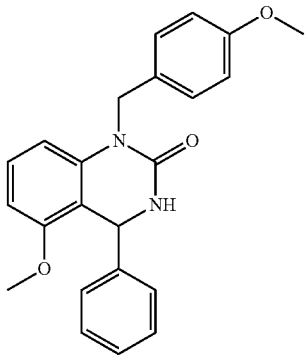 [SMILES: COc1ccc(CN2C(=O)NC(c3ccccc3)c3c(OC)cccc32)cc1]

A mixture of reagent 1 (3.1 g, 0.012 mol), PMB-Cl (2.29 g, 0.015 mol) and Cs$_2$CO$_3$ (7.95 g, 0.024 mol) in DMF (150 mL) is stirred and refluxed for 24 h. The mixture is extracted with EA and purified by column chromatography on silica gel using a petrol ether/ethylacetate gradient. This affords the desired product.

Yield: 3.70 g, (80%)

5-Methoxy-1-(4-methoxy-benzyl)-3-methyl-4-phenyl-3,4-dihydro-1H-quinazolin-2-one

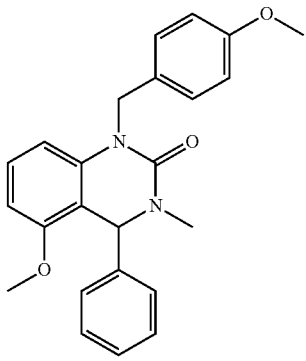 [SMILES: COc1ccc(CN2C(=O)N(C)C(c3ccccc3)c3c(OC)cccc32)cc1]

To a solution of 5-Methoxy-1-(4-methoxy-benzyl)-3-methyl-4-phenyl-3,4-dihydro-1H-quinazolin-2-one (3.50 g, 9.36 mmol) in DMF (150 mL) at 0° C. under nitrogen is added sodium hydride (0.27 g, 11.23 mmol) and stirred for 3 min, then methyl iodide (1.33 g, 9.35 mmol) is added. The resulting solution is stirred for 3 h. The reaction mixture is extracted into ethylacetate from water to give the desired product.

Yield: 3.10 g (85%)

5-Methoxy-3-methyl-4-phenyl-3,4-dihydro-1H-quinazolin-2-one

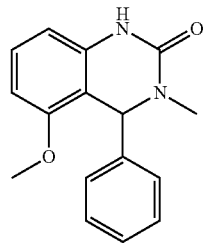 [SMILES: COc1cccc2c1C(c1ccccc1)N(C)C(=O)N2]

A solution of reagent 1 (2.00 g, 0.005 mol) in TFA (200 mL) and methoxybenzene (18 mL) is stirred and refluxed for 18 h. At the end of reaction, the mixture is evaporated and extracted into DCM from water to give the desired product.

Yield: 1.27 g (92%)

6-Bromo-5-methoxy-3-methyl-4-phenyl-3,4-dihydro-1H-quinazolin-2-one

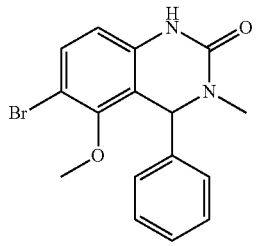 [SMILES: COc1c(Br)ccc2c1C(c1ccccc1)N(C)C(=O)N2]

A mixture of 5-Methoxy-3-methyl-4-phenyl-3,4-dihydro-1H-quinazolin-2-one (1.38 g, 0.005 mol) and NBS (0.82 g, 0.0046 mol) in DCM (150 mL) is stirred at r.t. for 4 h. The mixture is extracted with DCM from water and purified by column chromatography on silica gel using an ethylacetate and petrol ether gradient to give the desired product.

Yield: 1.20 g (71%)

HPLC-MS: M+H=347/349; $t_{Ret}$=2.82 min; AM5

6-(3,5-Dimethyl-isoxazol-4-yl)-5-methoxy-3-methyl-4-phenyl-3,4-dihydro-1H-quinazolin-2-one

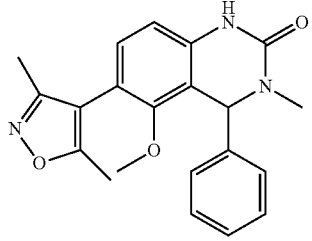 [SMILES: COc1c(-c2c(C)noc2C)ccc2c1C(c1ccccc1)N(C)C(=O)N2]

6-Bromo-5-methoxy-3-methyl-4-phenyl-3,4-dihydro-1H-quinazolin-2-one (200 mg, 0.576 mmol), 3,5-dimethyl-4-isoxazolylboronic acid (105.5 mg, 0.749 mmol), potassium tert-butoxide (129 mg, 1.152 mmol), 1,1'-bis(di-tert-butylphosphino)ferrocene palladium dichloride (75 mg, 0.115 mmol) are added to a microwave vial. Dimethoxyethane (0.5 mL) is added and the vessel flushed with argon and stirred in a microwave reactor at 90° C. for 90 min. The solvent is evaporated, the residue dissolved in acetonitrile/formic acid, and then purified by preparative HPLC.

Yield: 23 mg (11%)

HPLC-MS: M+H=364; $t_{Ret}$=1.12 min; AM1

Biological Methods

BRD4-H4 tetraacetylated peptide inhibition AlphaScreen

This assay is used to determine whether the compounds inhibit the interaction between the first (BRD4-BD1) or the second (BRD4-BD2) bromodomain of BRD4 and the tetraacetylated histone H4 peptide.

Compounds are diluted in serial dilution 1:5 in assay buffer from 10 mM stock in DMSO (100 µM start concentration) in white OptiPlate-384 (PerkinElmer). A mix consisting of 15 nM GST-BRD4-BD1 protein (aa 44-168) or 150 nM GST-BRD4-BD2 (aa 333-460) and 15 nM biotinylated Acetyl-Histone H4 (LysS, 8, 12, 16) peptide is prepared in assay buffer (50 mM HEPES pH=7.4; 25 mM NaCl; 0.05% Tween 20; 0.1% bovine serum albumin (BSA); 10 mM dithiothreitol (DTT)). 6 µl of the mix is added to the compound dilutions. Subsequently, 6 µl of premixed AlphaLISA Glutathione Acceptor Beads and AlphaScreen Streptavidin Donor Beads from PerkinElmer (in assay buffer at a concentration of 10 μg/ml each) are added and the samples are incubated for 30 min at RT in the dark (shaking 300 rpm). Afterwards, the signal is measured in a PerkinElmer Envision HTS Multilabel Reader using the AlphaScreen protocol from PerkinElmer. Each plate contains negative controls where biotinylated Acetyl-Histone H4 peptide and GST-BRD4-BD1 or GST-BRD4-BD2 are left out and replaced by assay buffer. Negative control values are entered as low basis value when using the software GraphPad Prism for calculations. Furthermore, a positive control (probe molecule JQ1+ with protein/peptide mix) is pipetted. Determination of $IC_{50}$ values are carried out using GraphPad Prism 3.03 software (or updates thereof).

Table summarizing the $IC_{50}$ of the compounds of the invention exemplified above

| EX # | IC50 [nM] |
|------|-----------|
| 1    | 44        |
| 2    | 27        |
| 3    | 66        |
| 4    | 31        |
| 5    | 38        |
| 6    | 225       |
| 7    | 105       |
| 8    | 75        |
| 9    | 68        |
| 10   | 423       |
| 11   | n.d.      |
| 12   | 241       |
| 13   | 119       |
| 14   | 90        |
| 15   | 837       |
| 16   | 166       |
| 17   | 252       |
| 18   | 76        |
| 19   | 31        |
| 20   | 213       |
| 21   | 825       |

On the basis of their biological properties the compounds of general formula (I) according to the invention, their tautomers, racemates, enantiomers, diastereomers, mixtures thereof and the salts of all the above-mentioned forms are suitable for treating diseases characterised by virus infection, inflammatory diseases and abnormal cell proliferation, such as cancer.

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon carcinoma, colorectal carcinoma, anal carcinoma, carcinoma of the large bowel, tumours of the small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas (NSCLC) such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma (MM)), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma such as for example vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva. Preferred cancers, which may be treated with compounds according to the invention, are hematopoietic malignancies (including but not limited to AML, MM), as well as solid tumors including but not limited to lung, liver, colon, brain, thyroid, pancreas, breast, ovary and prostate cancer.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (I) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosine kinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Other possible combination partners are 2-chlorodesoxyadenosine, 2-fluorodesoxycytidine, 2-methoxyoestradiol, 2C4, 3-alethine, 131-I-TM-601, 3CPA, 7-ethyl-10-hydroxy-camptothecin, 16-aza-epothilone B, A 105972, A 204197, aldesleukin, alitretinoin, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, ARRY-300, ARRY-142886/AZD-6244, ARRY-704/AZD-8330, AS-703026, azacytidine, azaepothilone B, azonafide, BAY-43-9006, BBR-3464, BBR-3576, bevacizumab, biricodar dicitrate, BCX-1777, bleocin, BLP-25, BMS-184476, BMS-247550, BMS-188797, BMS-275291, BNP-1350, BNP-7787, BIBW 2992(afatinib), BIBF 1120 (Vargatef), bleomycinic acid, bleomycin A, bleomycin B, bryostatin-1, bortezomib, brostallicin, busulphan, CA-4 prodrug, CA-4, CapCell, calcitriol, canertinib, canfosfamide, capecitabine, carboxyphthalatoplatin, CCI-779, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, clofarabin, colchicin, combretastatin A4, CHS-828, CLL-Thera, CMT-3 cryptophycin 52, CTP-37, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, E7010, E-6201, edatrexat, edotreotide, efaproxiral, eflornithine, EKB-569, EKB-509, elsamitrucin, epothilone B, epratuzumab, ER-86526, erlotinib, ET-18-OCH3, ethynylcytidine, ethynyloestradiol, exatecan, exatecan mesylate, exemestane, exisulind, fenretinide, floxuridine, folic acid, FOLFOX, FOLFIRI, formestane, galarubicin, gallium maltolate, gefinitib, gemtuzumab, gimatecan, glufosfamide, GCS-IOO, G17DT immunogen, GMK, GPX-100, GSK-5126766, GSK-1120212, GW2016, granisetron, hexamethylmelamine, histamine, homoharringtonine, hyaluronic acid, hydroxyurea, hydroxyprogesterone caproate, ibandronate, ibritumomab, idatrexate, idenestrol, IDN-5109, IMC-1C11, immunol, indisulam, interferon alpha-2a, interferon alfa-2b, interleukin-2, ionafarnib, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, lobaplatin, leflunomide, lenograstim, leuprolide, leuporelin, lexidronam, LGD-1550, linezolid, lutetium texaphyrin, lometrexol, losoxantrone, LU 223651, lurtotecan, mafosfamide, marimastat, mechloroethamine, methyltestosteron, methylprednisolone, MEN-10755, MDX-H210, MDX-447, MGV, midostaurin, minodronic acid, mitomycin, mivobulin, MK-2206, MLN518, motexafin gadolinium, MS-209, MS-275, MX6, neridronate, neovastat, nimesulide, nitroglycerin, nolatrexed, norelin, N-acetylcysteine, 06-benzylguanine, omeprazole, oncophage, ormiplatin, ortataxel, oxantrazole, oestrogen, patupilone, pegfilgrastim, PCK-3145, pegfilgrastim, PBI-1402, PEG-paclitaxel, PEP-005, P-04, PKC412, P54, PI-88, pelitinib, pemetrexed, pentrix, perifosine, perillylalcohol, PG-TXL, PG2, PLX-4032/RO-5185426, PT-100, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, RAF-265, ramosetron, ranpirnase, RDEA-119/BAY 869766, rebeccamycin analogues, revimid, RG-7167, rhizoxin, rhu-MAb, risedronate, rituximab, rofecoxib, Ro-31-7453, RO-5126766, RPR 109881A, rubidazon, rubitecan, R-flurbiprofen, S-9788, sabarubicin, SAHA, sargramostim, satraplatin, SB 408075, SU5416, SU6668, SDX-101, semustin, seocalcitol, SM-11355, SN-38, SN-4071, SR-27897, SR-31747, SRL-172, sorafenib, spiroplatin, squalamine, suberanilohydroxamic acid, sutent, T 900607, T 138067, TAS-103, tacedinaline, talaporfin, tariquitar, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymectacin, tiazofurin, tipifarnib, tirapazamine, tocladesine, tomudex, toremofin, trabectedin, TransMID-107, transretinic acid, traszutumab, tretinoin, triacetyluridine, triapine, trimetrexate, TLK-286TXD 258, urocidin, valrubicin, vatalanib, vincristine, vinflunine, virulizin, WX-UK1, vectibix, Volasertib (or other polo-like kinae inhibitors), xeloda, XELOX, XL-281, XL-518/R-7420, YM-511, YM-598, ZD-4190, ZD-6474, ZD-4054, ZD-0473, ZD-6126, ZD-9331, ZDI839, zoledronat and zosuquidar.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) | Tablets | per tablet |
|---|---|---|
| | active substance according to formula (I) | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance according to formula (I) | 80 mg |
| | lactose | 55 mg |
| | corn starch | 190 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | Ampoule solution | |
|---|---|---|
| | active substance according to formula (I) | 50 mg |
| | sodium chloride | 50 mg |
| | water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of formula (I)

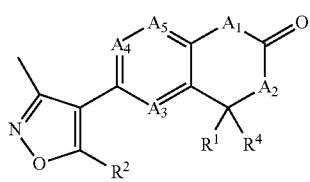

(I)

wherein, $A_1$ is —NH—, or —N($C_{1-3}$alkyl)- ;

$A_2$ is —N—$C_{1-3}$alkyl , wherein —$C_{1-3}$alkyl is optionally substituted with $R^5$;

$A_3$ is —N— or —C($R^3$)—, $A_4, A_5$ is independently —N— or —CH—;

$R^1$ is 6 membered heteroaryl or phenyl, both of which groups can be optionally and independently substituted with halogen;

$R^2$ is —H, —$C_{1-3}$alkyl or —O—$C_{1-3}$alkyl;

$R^3$ is —H or —O—$C_{1-3}$alkyl;

$R^4$ is —H or —$CH_3$;

$R^5$ is a 6 membered heterocycle or phenyl, each of which groups can be optionally substituted with —O—$C_{1-3}$alkyl or —$C_{1-3}$alkyl;

or a pharmaceutically acceptable salt thereof.

2. The compound according to claim 1, wherein $A_1$ is —NH— or —N($CH_3$)—.

3. The compound according to claim 2, wherein $A_1$ is —NH—.

4. The compound according to claim 1, wherein $A_2$ is selected from —N($CH_3$)—, —N(—$CH_2$(piperidinyl))-, —N(—$CH_2$(tetrahydrofuranyl))- , —N(benzyl)-, wherein the benzyl is optionally substituted with —O—$CH_3$ and wherein the piperidinyl is optionally substituted with —$CH_3$.

5. The compound according to claim 1 wherein R1 is pyridyl or phenyl, wherein phenyl is optionally substituted with halogen.

6. The compound according to claim 1, wherein $A_3, A_4$ and $A_5$ are —CH—.

7. A compound selected from

| EX# | Structure |
|---|---|
| 1 | |
| 2 | 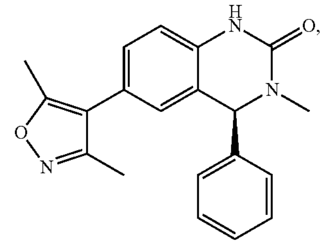 [SMILES: Cc1noc(C)c1-c1ccc2c(c1)[C@H](c1ccccc1)N(C)C(=O)N2] |
| 3 | 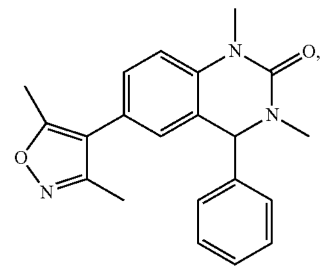 [SMILES: Cc1noc(C)c1-c1ccc2c(c1)C(c1ccccc1)N(C)C(=O)N2C] |
| 4 | 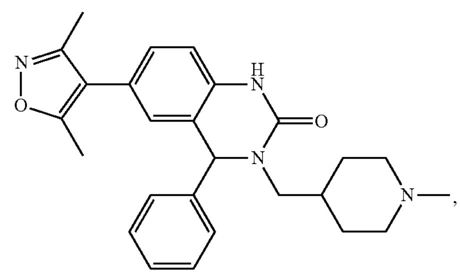 [SMILES: Cc1noc(C)c1-c1ccc2c(c1)C(c1ccccc1)N(CC1CCN(C)CC1)C(=O)N2] |
| 5 | 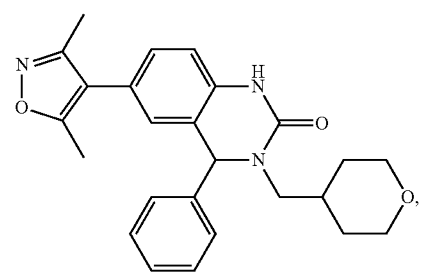 [SMILES: Cc1noc(C)c1-c1ccc2c(c1)C(c1ccccc1)N(CC1CCOCC1)C(=O)N2] |
| 6 | 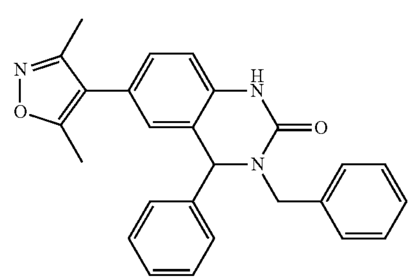 [SMILES: Cc1noc(C)c1-c1ccc2c(c1)C(c1ccccc1)N(Cc1ccccc1)C(=O)N2] |

-continued

| EX# | Structure |
|---|---|
| 7 | (structure) |
| 13 | (structure) |
| 15 | (structure) |
| 16 | (structure) |
| 17 | (structure) |

-continued

| EX# | Structure |
|---|---|
| 18 | (structure) |
| 19 | (structure) |
| 20 | (structure) |
| 21 | (structure) and | or a pharmaceutically acceptable salt thereof.

8. A pharmaceutical composition comprising a therapeutically effective amount of a compound of the formula (I) according to claim 1 optionally in combination with pharmaceutically acceptable excipients and/or carriers.

9. The pharmaceutical composition according to claim 8 further comprising at least one other cytostatic or cytotoxic active substance, different from formula (I).

* * * * *